(12) United States Patent
Kumar

(10) Patent No.: US 10,194,961 B2
(45) Date of Patent: Feb. 5, 2019

(54) PROSTHESIS

(71) Applicant: Pranesh Kumar, Rotorua (NZ)

(72) Inventor: Pranesh Kumar, Rotorua (NZ)

( * ) Notice: Subject to any disclaimer, the term of this patent is extended or adjusted under 35 U.S.C. 154(b) by 0 days.

(21) Appl. No.: 15/355,807

(22) Filed: Nov. 18, 2016

(65) Prior Publication Data
US 2017/0196603 A1 Jul. 13, 2017

Related U.S. Application Data

(63) Continuation-in-part of application No. 13/514,239, filed as application No. PCT/NZ2010/000211 on Oct. 21, 2010.

(60) Provisional application No. 61/253,907, filed on Oct. 22, 2009.

(51) Int. Cl.
*A61F 2/38* (2006.01)
*A61B 17/80* (2006.01)
*A61B 17/56* (2006.01)

(52) U.S. Cl.
CPC .... *A61B 17/8061* (2013.01); *A61B 2017/567* (2013.01); *A61B 2017/568* (2013.01)

(58) Field of Classification Search
CPC ............... A61B 17/80; A61B 17/6425; A61B 2017/567; A61F 2/3859; A61F 2/389
See application file for complete search history.

(56) References Cited

U.S. PATENT DOCUMENTS

2009/0318976 A1* 12/2009 Gabriel ................. A61B 17/56
606/283

* cited by examiner

*Primary Examiner* — Brian Dukert
(74) *Attorney, Agent, or Firm* — Tarolli, Sundheim, Covell & Tummino LLP

(57) ABSTRACT

Osteoarthiritis (OA) is the most common disease affecting human joints. Mechanical stress through the joint is one of the most important independent etiological factors. The present invention provides a prosthesis that by passes some of the stress from the joint without destroying the joint surface. It allows may provide a full range of joint movement, while sharing the load with the physiological joint, thereby maintaining the viability of the physiological joint surface. In addition, the prosthesis can accommodate native soft tissue structures in or around the joint, such as ligaments.

14 Claims, 23 Drawing Sheets

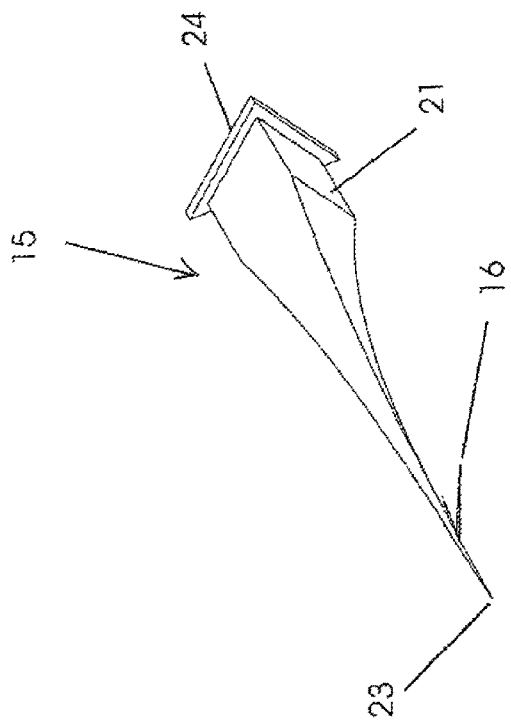
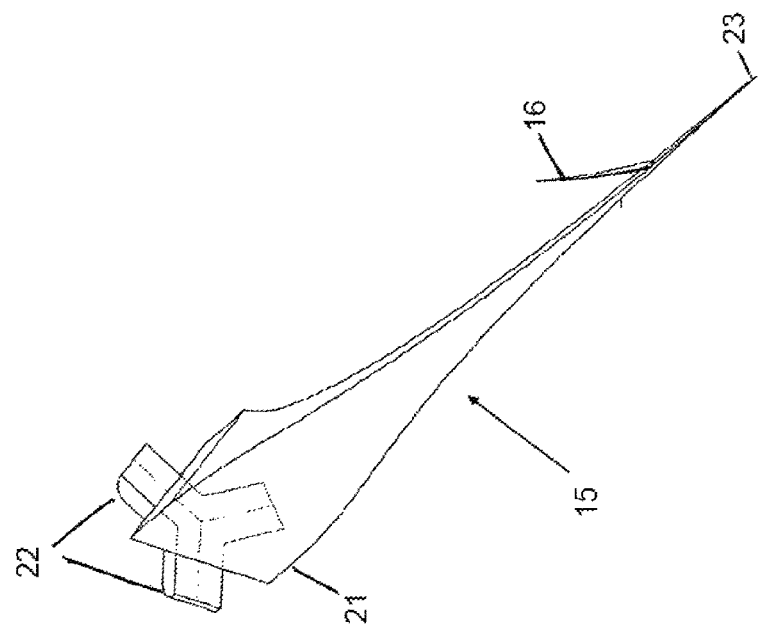

PROSTHESIS

STATEMENT OF CORRESPONDING APPLICATIONS

This application is a continuation-in-part of U.S. Non-Provisional patent application Ser. No. 13/514,239, filed on Jun. 6, 2012, which is a U.S. National Stage application under 35 USC 371 of PCT Application Serial No. PCT/NZ2010/000211, filed on Oct. 21, 2009, which claims priority to U.S. Provisional Patent Application No. 61/253,907 the entire contents of all of which are incorporated herein by reference.

TECHNICAL FIELD

The present invention relates to a prosthetic device which is surgically implantable into a body joint to support the joint.

BACKGROUND ART

Osteoarthritis (OA) is the most common disease affecting human joints. It is second only to cardiovascular disease as the cause of chronic disability in adults. Worldwide, billions of dollars are spent annually for its treatment and for the lost days in work.

OA is widely considered to be a degenerative joint disease and more than 50% of individuals above the age of 65 years have clinical evidence of OA. Nevertheless, OA cannot be described as a simple consequence of aging. Epidemiological studies have shown a strong correlation of OA with obesity, physical sports and occupation. Moreover, mechanical stress through the joint has been suggested as one of the most important independent etiological factors.

While physiological stress is needed for cartilage and bone sustenance and repair, excessive stress through joint surface leads to initiation and progression of OA. Prolonged high stress and excessive impulsive stress are detrimental to cartilage viability, whereas repetitive physiological stress is beneficial for cartilage health.

Patients with OA generally present with pain, stiffness and deformity of the joint. Present treatment protocols are mainly symptomatic treatment. Initial management of most patients includes changes in lifestyle, Non-Steroidal Anti-Inflammatory Drugs (NSAIDs), analgesics, physical therapy, bracing and ambulatory aids. Surgical treatment is indicated only when consecutive treatment fails to improve the symptoms.

With particular reference to the knee common surgical options include arthroscopic debridement, high tibial osteotomy (HTO), and unicompartmental or tricompartmental knee replacement. In general, present forms of joint replacement surgery completely sacrifice the natural joint and only provide limited symptom relief and restricted mobility. Further, the lifespan of the replaced joint is also limited. None of the presently available treatment methods change the natural progress of the disease.

It is known to provide knee implants. One example of such a device is disclosed in United States Patent Publication No. 2008/0275561 A1 to Exploramed NC4, Inc. The patent discloses various implants used for absorbing energy between body parts, and in particular knee joints.

The implants disclosed in the Exploramed patent are intended to absorb energy when the knee is extended (e.g. the leg is straight). That energy is absorbed by an energy manipulator such as a spring or elastomeric material. The energy is subsequently distributed into the localised knee area on flexion of the knee (e.g. bending of the leg). However, the configurations of the implants of the Exploramed patent only rely on the native knee joint to provide the range of motion for knee movement. That is, the ends of the tibia and femur bones continue to provide articulation of the knee. This limits effectiveness of the disclosed devices as it will affect the natural mechanism of the knee joint such as by creating an unnatural arc of motion.

An implant must also be positioned inside the body e.g. inside or adjacent to a joint. However, the implant may interact with parts of the joint such as the ligaments which hold the bones of the joint together. For instance, an implant could lie overtop of, or otherwise rub, the ligaments, and/or could restrict the ligaments as the joint moves through a native range of motion. This is a particularly difficult issue to address because the ligaments around the knee are complex, and the shape, orientation and direction of these change as the knee flexes. These issues can reduce or limit the effectiveness of the implant(s), or its suitability for use in treating certain conditions.

It is an object of the present invention to provide an improved implant and method of employing same.

It is also an object of the invention to provide an implant which may be more easily implanted to a patient.

It is yet a further object of the invention to provide an implant which may reduce or minimise the adverse effects on the native knee joint when implanted therein.

Yet a further object of the invention is to provide an implant which reduces undesirable interactions with ligaments and muscles forming part of, or adjacent to, a joint.

In addition, it is an object of the present invention to address the foregoing problems or at least to provide the public and medical profession with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

DISCLOSURE OF THE INVENTION

According to one aspect of the present invention, there is provided a prosthesis for insertion into a joint, including a first plate configured for fixing to a first bone forming part of the joint, wherein the first plate is configured to accommodate one or more of the native ligaments in or around the joint.

According to another aspect of the present invention, there is provided a prosthesis for insertion into a patient's knee joint, including a first plate that has a deep surface and a superficial surface, wherein the deep surface is shaped to conform to at least a portion of the lateral margin or at least a portion of the medial margin of a bone forming part of the patient's knee joint.

According to another aspect of the present invention there is provided a prosthesis, including a first lateral plate that is shaped to conform to at least a portion of the antero-lateral margin of the patient's femur and a second lateral plate that is shaped to conform to at least a portion of the antero-lateral margin of the patient's tibia, a first medial plate that is shaped to conform to at least a portion of the antero-medial margin of the patient's femur and a second medial plate that is shaped to conform to at least a portion of the antero-medial margin of the patient's tibia, wherein at least one of the first lateral plate or the first medial plate is configured to in-use accommodate one or more of the native ligaments in or around the patient's knee joint.

According to another aspect of the present invention, there is provided a prosthesis for insertion into a joint, including a first plate configured for fixing to a first bone forming part of the joint, wherein the first plate includes an articulating surface, a second plate configured for fixing to a second bone forming part of the joint, wherein the second plate includes an articulating surface, and further wherein the respective articulating surfaces are shaped to in use cooperate with each other to guide movement of the second bone relative to the first bone through a desired range of motion.

According to another aspect of the present invention, there is provided a method of implanting a prosthesis in a joint, including the following steps in any order:
  (a) aligning a first plate including an articulating surface with a first bone forming part of the joint;
  (b) securing the first plate to the first bone;
  (c) aligning a second plate including an articulating surface with a second bone forming part of the joint;
  (d) securing the second plate to the second bone;
    wherein the method ensures that the articulating surfaces can in use co-operate with each other to guide movement of the second bone relative to the first bone through a desired range of motion.

A prosthesis kit, including
  (a) a first plate configured for fixing to a first bone forming part of a joint;
  (b) a second plate configured for fixing to a second bone forming part of the joint;
    wherein each of the first plate and second plate have articulating surfaces that are shaped to co-operate with each other when the prosthesis is fitted into the joint so as to guide movement of the second bone relative to the first bone through a desired range of motion.

According to another aspect of the present invention, there is provided a fastener for fixing a prosthetic structure to bone, including
  a body with a length,
  a first point end,
  a second end distal to the first end
  wherein the second end is configured to facilitate inserting the fastener into bone, and wherein
  the body has a section with a generally triangular cross section.

In an embodiment, the present invention may aim to alter the etio-pathogenesis of OA, by providing a mechanism to partially bypass the stresses experienced by a joint (articulating) surface(s). In a preferred embodiment this is achieved by sharing the load with the native joint surface. The implant of the invention assists the joint to bear the prolonged constant high stress and excessive impulsive stresses that are detrimental to joint physiology, while maintaining some physiological stress to be transferred through the native joint surface.

It should be appreciated that the term "desired range of motion" refers to the preferred motion path as well as the angle of movement.

In a preferred embodiment, the desired range of motion is a functional range of motion for the joint.

In a particularly preferred embodiment, the joint may be guided to move as it is physiologically designed to do so, and preferably with a full range of normal movement e.g. maximum extension/flexion, and/or pronation/supination.

Importantly, a prosthesis according to the present may provide a full range of motion of the treated joint which corresponds to the native joint. At the same time, the prosthesis may protect the native bones forming the joint, while potentially providing symptomatic relief, improved joint recovery and improved function. The present prosthesis can also be applied using a relatively smaller operation than total joint replacements, or in the case of a knee prosthesis the High Tibial Osteotomy (HTO).

In a preferred embodiment the present invention is intended for use in joints including knees, elbows, ankles, fingers, shoulders, wrists, or hips. Various exemplary joints including embodiments will be discussed herein. However the discussion of these embodiments should not be seen as limiting and alternatives are envisaged.

Throughout the present specification reference will be made to the first bone of a joint and the second bone of a joint. These terms should be given their ordinary meaning as would be known to those skilled in the art. For instance, in the embodiment of a knee prosthesis the first bone is the femur while the second bone is the tibia. In a hip prosthesis the first bone is the pelvis while the second bone is the femur.

Certain joints may include third bones such as the radius of the elbow.

Embodiments of the present to account for such joints are discussed below.

Throughout the present specification the term first plate or second plate should be understood as meaning components having a width and which are configured for fixing to a first or second bone.

In a preferred embodiment the first and/or second plates have a deep surface that is shaped to conform to at least part of a surface of a bone to which the plate will be attached. This may facilitate the force placed on the prosthesis to be distributed more evenly with respect to the joint, rather than creating points of concentrated pressure. The prosthesis may also be more compact and better suited for insertion into the joint.

The first and/or second plates also have a superficial surface, which is on the distal side of the deep surface from the bone. In other words, the deep surface is the surface of a plate which is closest to the bone to which the plate is attached in use, while the superficial surface of the plate is the surface distal to the surface of the bone. The distance between the deep surface and the superficial surface defines a thickness for the plate(s). It should also be appreciated that the thickness of the plate(s) may vary.

The present invention may also include more than two plates. This will depend on the particular joint with which a prosthesis is used. For instance in an elbow or shoulder joint, a third plate (and even potentially a fourth plate), could be secured to bones forming the joint such as to facilitate movement of the joint through a desired range of motion. In the case of an elbow joint the second plate may be secured to the ulna and the third plate secured to the radius. Each of the plates may have a bearing surface that cooperates with a corresponding bearing surface on one or more plates secured to the humerus.

It is also envisaged that the prosthesis could be provided by two pairs of plates. For instance, in a knee joint, a pair of plates could be fixed to the lateral margins of a knee joint (a pair of lateral plates) and a second pair of plates could be fixed to the medial margins of a knee joint (a pair of medial plates). In this embodiment, the articulating surfaces of each pair of plates are shaped so as to conform to, and/or mimic, the shape of condyles of bones forming the knee joint.

In a preferred embodiment, the plates may be shaped and/or otherwise configured to facilitate its insertion into a joint while accommodating the joint's native ligaments.

For instance, a plate may have an aperture or opening that extends from the deep surface to the superficial surface. When the plate is inserted into a joint and positioned relative to a bone of the joint, at least one native ligament in or around the joint can extend through the aperture.

In addition, the aperture may be unbounded at an edge which can facilitate the plate being inserted into the joint and the ligament(s) to extend from through the aperture. This will allow the plate to be twisted around the ligament(s) before being secured in position to the native bone.

It is also envisaged that a plate according to an embodiment of the invention is shaped and configured to slide under and extend along a ligament of a joint. For instance, a tibial plate may have a first portion which extends along the sagittal plane (e.g. anterior to posterior) and a portion which extends along the vertically (e.g. proximate to distal). The first portion can lie underneath a/the ligament, which may enable the plate to provide an articulating surface while also accommodating the native ligament(s). The second portion also accommodates the ligament(s) by reducing irritation or touching of these completely. However, the second portion provides an increase surface area to attach to the tibia and therefore may facilitate better load distribution into the tibia at locations away from the articulating surfaces.

Alternatively, a plate according to the invention may be provided by two or more components. In use, the first component of the plate is positioned relative to the joint so that the ligament(s) is/are positioned in an aperture in the first component. A second component of the plate is positioned relative to the first component, the first and second components are attached to the bone, such as using fasteners described herein, or any other suitable fastener.

These features help to secure the plates in position without the necessity of cutting the native ligaments. This may promote patient rehabilitation. In addition, the aperture may provide advantages such as enabling the joint to move through a desired-range of motion while minimizing or substantially eliminating irritation to the ligament(s).

Yet a further advantage that may be provided by the advantage is that, as the prosthesis accommodates the native ligament(s) in and around the joint that the ligaments can continue to perform their normal functions. For instance, the ligament(s) can act to hold the bone while muscle move the bones of the joint. That is, action of the ligament(s) is/are substantially unaffected by the presence of the plate(s).

In an embodiment, the first component of the plate and a second component of the plate may be connected together in vivo, such as when a prosthesis according to the invention is fitted to a patient. However, it is also envisaged that the plate sub-parts may be connected to each prior to implantation to a patient.

In an embodiment, it is envisaged that the first plate component and second plate component may have features or structure to align them with respect to each other and/or attach them together. For instance, the first plate component may have channel(s) and/or protrusion(s) while the second plate component may have channel(s)/protrusion(s), and the respective channel(s) and/or protrusion(s) engage each other.

It is also envisaged that the features or structure may prevent or restrict movement of the components with respect to each other in one direction only. Additional movement of the plate components in other planes/directions may be restricted by fasteners as described herein.

The articulating surface(s) may facilitate transferring weight or force applied to a joint substantially away from the native joint articulating surface. This may enable the plates to transfer the force to the bones surrounding the joint. For instance, in a knee prosthesis embodiment of the invention, the plates may be secured to the antero-lateral and/or antero-medial margins of the native bones forming the knee joint, and therefore interaction of the articulating surfaces assists to transfer weight/force to the antero-lateral and/or antero-medial margins of the native bones.

In addition, the articulating surfaces also facilitate the first plate and second plate, and therefore the bones forming the joint, moving with respect to each other. This may be provided by the articulating surfaces having low frictional coefficients so that they can slide relative to each other. Alternatively, ball bearings or other components may be provided between the articulating surfaces so as to allow these to move with respect to each other. This is useful is providing a joint with a desired range of motion.

In the preferred embodiment the articulating surfaces cooperate so as to guide the movement of the bones forming the joint with respect to each other. This is achieved by providing at least one of the articulating surfaces with a shape corresponding to the desired range of motion.

In a particularly preferred embodiment, at least one of the articulating may have a shape corresponding to an articulating surface of a natural joint. For instance, an articulating surface of a knee prosthesis may be shaped so as to conform to, or mimic, the condyles of the femur. This articulating surface is a complex shape, having a series of involute midpoints generally falling on a spiral. The cooperating articulating surface is shaped to correspond to the condyles of the tibia.

Alternative embodiments of the articulating surfaces will be discussed in more detail below by reference to different embodiments of prosthesis according to the present invention.

It is also envisaged that the articulating surfaces can be shaped to provide a desired range of motion other than that of native joint.

In yet a further embodiment, the articulating surfaces may be shaped so as to provide a range of motion for the joint corresponding to that of a native joint, yet have a shape which does not correspond to the articulating surfaces of that native joint. For instance, in an embodiment of an ankle joint, articulating surfaces of first and second plates define a range of motion corresponding to an arc of motion of the native joint, yet have shapes that do not correspond to the articulating surfaces of the ankle joint. Accordingly, the foregoing should not be seen as limiting on the scope of the present invention.

These aspects of the present invention should become clearer from the following description.

In a preferred embodiment, the prosthesis according to the present invention are configured to maintain separation (offloading) of the native bones forming a joint. This may allow the articulating surfaces of the prosthesis to facilitate the desired range of motion while minimising aggravation to those surfaces. That is, the articulating surfaces act as and provide, a track and guide for the bones to move without relying on the native joint surfaces. Note that the movement of the bones occurs by (or over) the articulating surfaces touching each other, rather than the native joint surfaces. These aspects of the present invention should become clearer from the following discussion of the preferred embodiments of the present invention.

Various embodiments are envisaged for the track and guide aspects of the articulating surfaces. For instance, articulating surfaces may be members and channels/grooves. Alternatively, a track may be a concave channel having a curve within which an elongate convex articulating surface can move.

Alternatively, ball and socket type arrangements are envisaged.

Yet a further embodiment of a track and guide envisaged as being within the scope of the present invention is a recess having a shelf or lip. Such an arrangement provides an articulating surface having a shape corresponding to the desired range of motion. A corresponding articulating surface cooperates with the recess and shelf/lip. Accordingly, the foregoing should not be seen as limiting.

Throughout the present specification reference to the term "range of motion" should now be understood as meaning the distance and direction of movement of two or more bones forming a joint with respect to each other.

In a preferred embodiment the desired range of motion is a normal range of motion of a joint. That range of motion will vary between different types of joints according to each joints' native characteristics. For instance, in a knee prosthesis the present invention will allow the femur and tibia bones to move with respect to each other through a normal range of flexion and extension. The prosthesis enables the bones to rotate to accommodate locking of the knee at extension.

In an alternate embodiment such as an elbow joint, the prosthesis can provide flexion and extension of the joint according to normal movement of the ulna and humerus. The prosthesis also facilitates rotational movement of the radius that occurs during pronation or supination of the forearm.

However the foregoing should not be seen as limiting as alternatives are envisaged including those where the prosthesis provides a range of motion less than a full range for a native joint. This may be beneficial where joint mobility is to be restricted to account for a medical condition or limitations of another joint/limb.

In a preferred embodiment, the prosthesis according to the present invention are configured to transfer some of the stress to which the joint is exposed into cartilage of the joint. This may be achieved by the relative spacing or interaction of the first plate and second plate, and/or their respective articulating surfaces.

Alternatively, a deformable component may be utilised. The deformable component allows movement of the first plate and second plate towards each other. However, the deformable component maintains sufficient separation of the native bones forming the joint such that these do not touch each other and articulation of the joint occurs via the bearing surfaces.

According to another aspect of the invention, there is provided a prosthesis for complete or partial insertion into the articular capsule of a patient's knee joint. For instance, the plate(s) as described herein may be positioned between the knee and the synovial membrane which contain the patella, ligaments, menisci and bursae of the knee joint. Similarly, alternate embodiment of the invention may or may not be located within the capsule of the respective joint. In these embodiments, the plate(s) are able to accommodate the native ligaments of the knee joint and therefore may facilitate movement of the knee joint as substantially described herein.

Having the component(s) of a prosthesis according to the invention inside the capsule also facilitates use of the space in the native joint to provide the prosthesis, and therefore assist with providing a low profile or less obtrusive implant.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages the construction and use of alternatives, of which the following gives examples only.

BRIEF DESCRIPTION OF THE DRAWINGS

Further aspects of the present invention will become apparent from the ensuing description which is given by way of example only and with reference to the accompanying drawings in which:

FIG. 8A is a perspective view of a fastener pin.

FIG. 8B is a perspective view of an alternate embodiment of a fastener pin.

FIGS. 22A-E are lateral side views of a patient's left knee showing a prosthesis according to the present invention facilitating movement between extension and flexion.

BEST MODES FOR CARRYING OUT THE INVENTION

The prosthesis, methods of implantation and fixation will now be described in more detail with reference to the drawings. Specific discussion of the embodiment of the prosthesis in respect of a knee joint is provided below. Substantively similar principles apply to the components of the knee prosthesis as they do to prosthesis used in other joints such as the ankle, finger, elbow, or shoulder. One skilled in the art would appreciate that the discussion in respect of the knee prosthesis is equally applicable in respect of other joints.

The present invention may be provided as a kitset of parts, including any one or more of the components described herein. It is envisaged that a kitset for an ankle, shoulder, elbow, finger or hip prosthesis could include components based on those described with reference to the knee prosthesis.

Knee Prosthesis

Referring first to FIGS. 1 to 9C, a preferred embodiment will be described in detail which utilises a pair of plates on the medial side of the knee joint ("the medial pair of plates") and a pair of plates on the lateral side of the joint ("the lateral pair of plates"). However, it should be appreciated that only one side of the joint (e.g. the medal or the lateral side) could be treated with the present invention.

Figure 1:
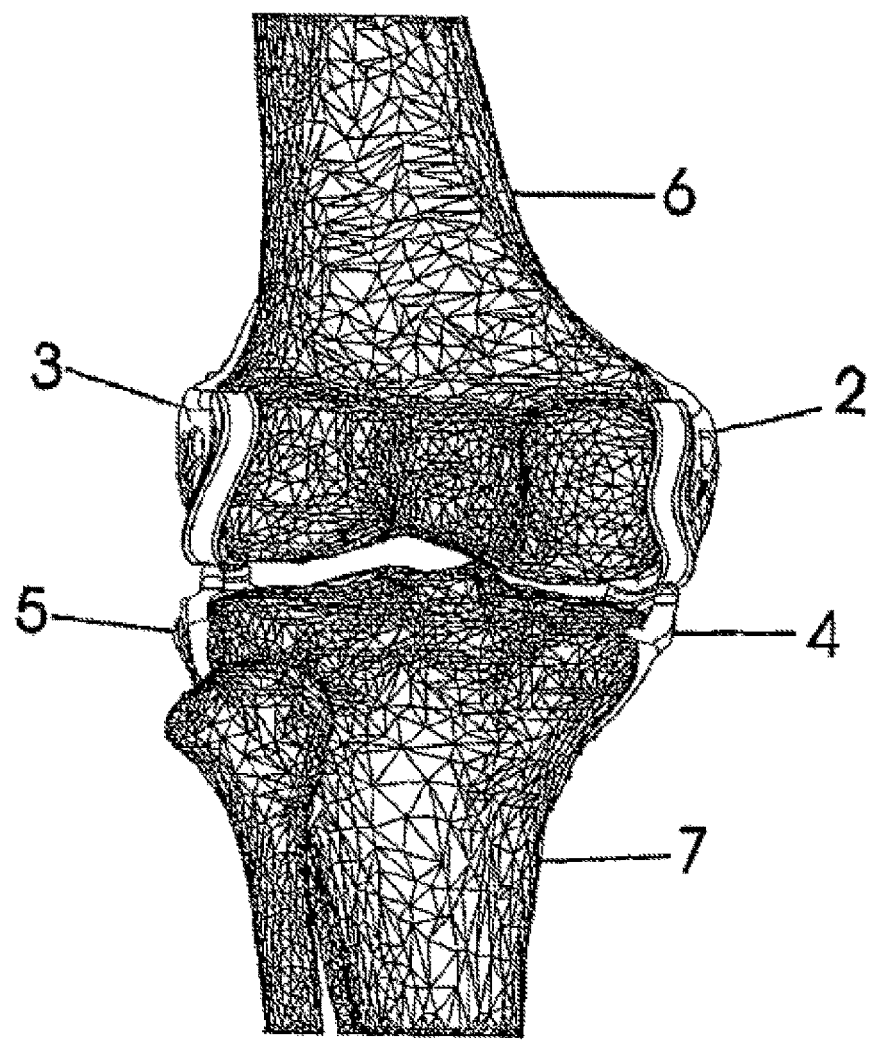
FIG. 1 is a back view of the prosthesis in situ, attached to a knee joint.
Figure 2:
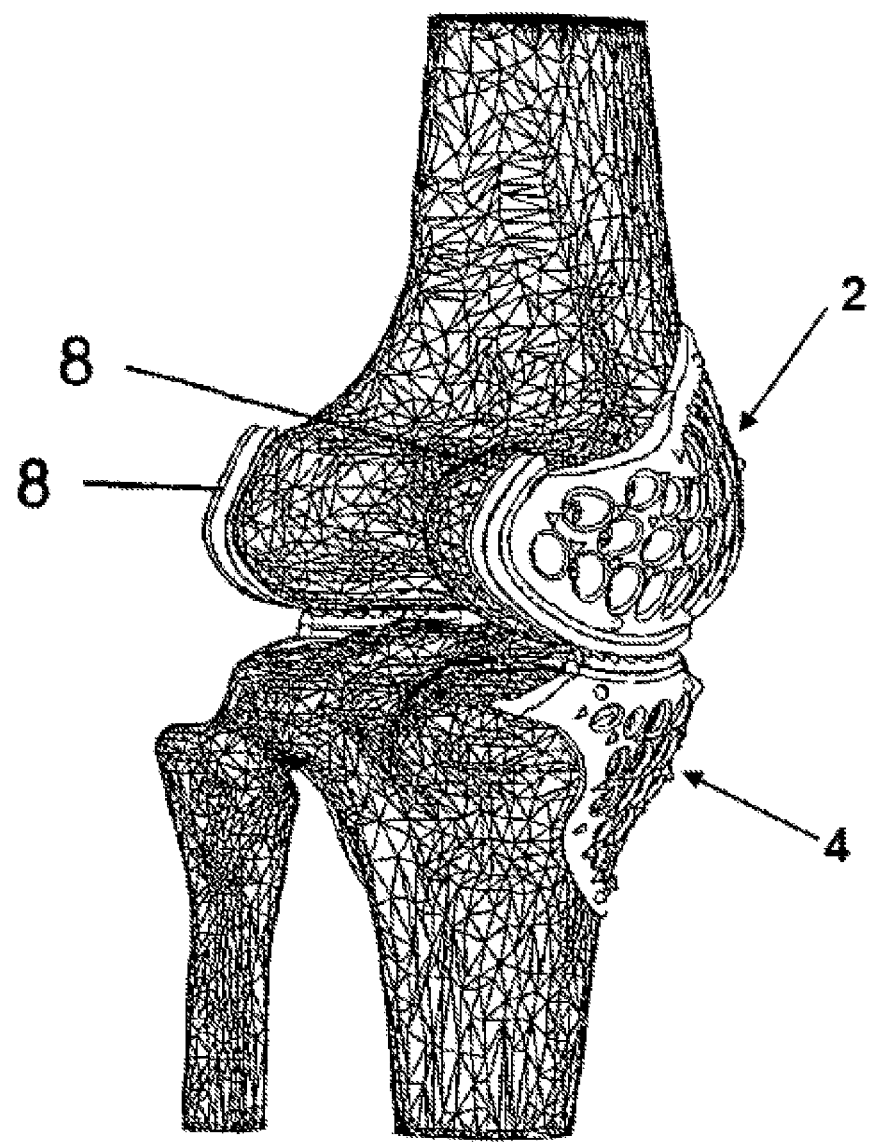
FIG. 2 is a rear perspective view of the joint and prosthesis shown in FIG. 1.
Figure 3:
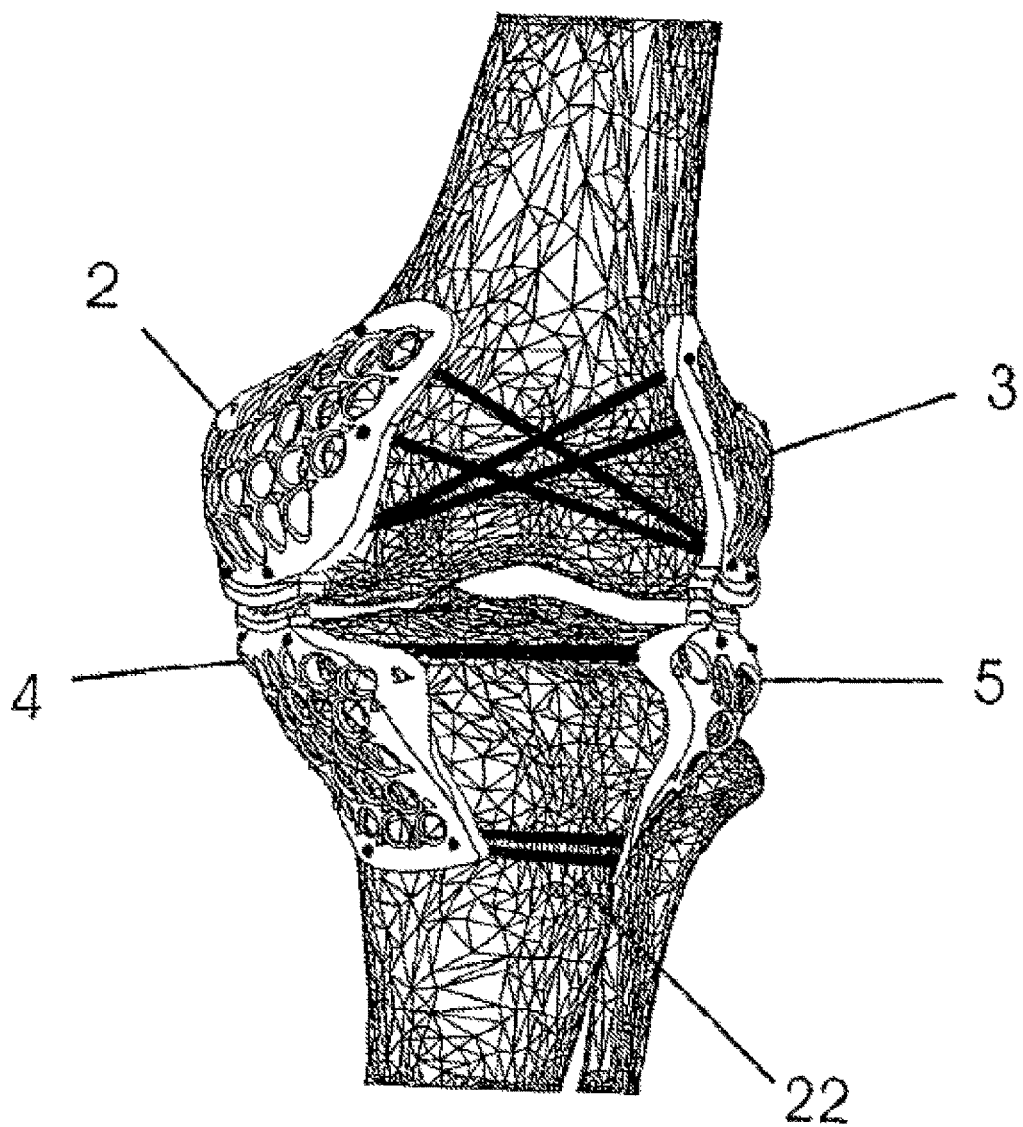
FIG. 3 is a front view of the prosthesis and knee joint shown in with cross rods inserted.

The lateral pair of plates includes a femoral plate 2 and a tibial plate 4, while the medial pair of plates includes a femoral plate 3 and a tibial plate 5. The prosthesis is provided for implantation into a knee joint and is attached directly to the surfaces of the distal femur and proximal tibia as generally illustrated in FIGS. 1-3.

The prosthesis is a low profile structure, being widest at the joint end and becomes progressively narrower further away from joint. The prosthesis allows space for important soft tissue structures including ligaments around the joint.

Each femoral plate 2, 3 and tibial plate 4, 5 may have a different shape and/or configuration depending on the condoyle of the femur or tibia to which it is to be attached i.e. each component may be configured according to the anatomical specificity of the bone involved ensuring a good fit. For instance, as is shown in FIGS. 1-3:

Femoral plates 2, 3 are shaped to conform to the antero-lateral and antero-medial distal end of the femur respectively. In particular, the femoral plate 2 has a deep surface which confirms to a surface of the antero-lateral distal end of the femur, while femoral plate 3 has a deep surface which conforms to the antero-medial distal end of the femur.

Tibial plates 4, 5 are shaped to conform to the antero-lateral and antero-medial proximal end of the tibia respectively. Accordingly, the tibial plate 2 has a deep surface which conforms to a surface of the antero-lateral proximal end of the tibia, while tibial plate 4 has a deep surface which conforms to the antero-medial proximal end of the tibia.

In the embodiment illustrated in FIGS. 1-3 the femoral plate 3 wraps around the lateral prominence of the femur while the femoral plate 2 wraps around the medial prominence of the femur.

The femoral plates 2, 3 are each generally tear drop shaped, with the anterior end being wider than posterior end in the direction of the sagittal plane. Therefore, each of the femoral plates 2, 3, wrap around the antero-lateral and antero-medial margins of the respective condoyle of the femur.

The tibial plates 4, 5 are each generally "L" shaped, having a first portion which extend generally along the transverse plane of the knee joint, and a second portion extend generally along a sagittal plane through the knee joint. The first portion of each tibial plates extends posteriorly to fit underneath the medial collateral ligament and the lateral collateral ligament respectively. This is best seen in FIGS. 20A-20D. As a result, the tibial plates 4, 5 accommodate the native ligament of the knee joint.

The second portion is orientated to extend generally downwards along the length of the tibia, and to be positioned adjacent to the medial or lateral collateral ligaments (as the case may be).

Articulating surfaces are provided on the distal margins of the femoral plates 2, 3 and on the proximal margins of the tibial plates 4, 5 to allow movement of the joint. The inner (deep) edges of the articulating surfaces of the femoral plates approximately follow the lateral/medial borders of the native joint articulating surfaces respectively. However, as can be seen in FIGS. 1, 2 & 3, the femoral plates 2, 3, and the tibial plates 4, 5, and/or the respective articulating surfaces, takes the natural space available between the ligament and bone and do not substantially extend into the medial or lateral compartments of the knee joint. However, the plates and/or articulating surfaces span the gap between the condoyles of the femur and tibia, to assist with completely or partially separating the native articulating surfaces of the joint (if required).

As shown in FIGS. 1 and 2 (and as is discussed in more detail below) the articulating surfaces of the plates are shaped so that they provide a desired range of motion for the native knee joint.

The articulating surfaces are broader posteriorly to accommodate the rotation and sideway motion of the knee in flexion. The articulating surface is slightly concave to allow for the rotation and locking of the knee in extension.

Accordingly, a portion of the total load applied through the joint is carried by the prosthesis along the medial and lateral margins of the native joint structure.

In a preferred embodiment, articulating surfaces are provided by separate articulating components 8A, 8B which are attached to distal edges of the femoral plates 2, 3 at or towards posterior edge. It is also envisaged that the articulating surfaces could be formed integrally into the femoral plates 2, 3.

Figure 9A:
FIG. 9A is an anterior view of lateral and medial femoral articulating components.
Figure 9B:
FIG. 9B is a posterior view of FIG. 9A.
Figure 9C:
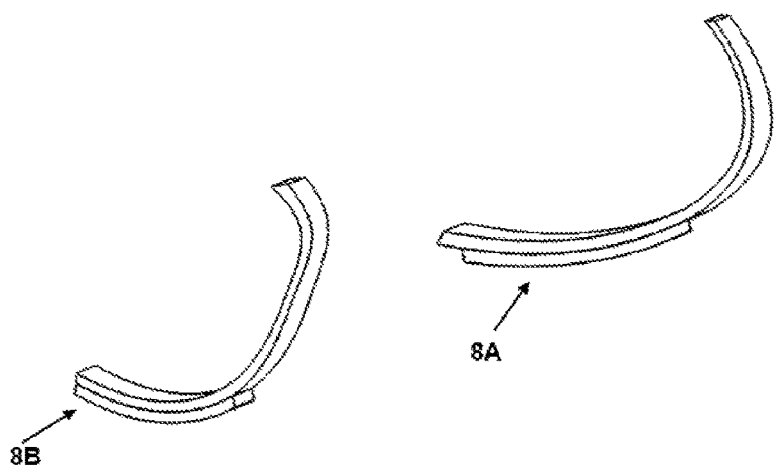
FIG. 9C is a perspective view of the components of FIGS. 9A and 9B.

Referring to FIG. 9A which show views of an articulating component 8A of a lateral femoral plate and an articulating component 8B of a medial femoral plate. The articulating components 8A, 8B provide articulating surfaces for the femoral plates 2, 3.

In a preferred embodiment, the femoral articulating components 8A, 8B each comprise a steel backed ultra-high density ceramic material to improve its wear characteristics.

Figure 5A:
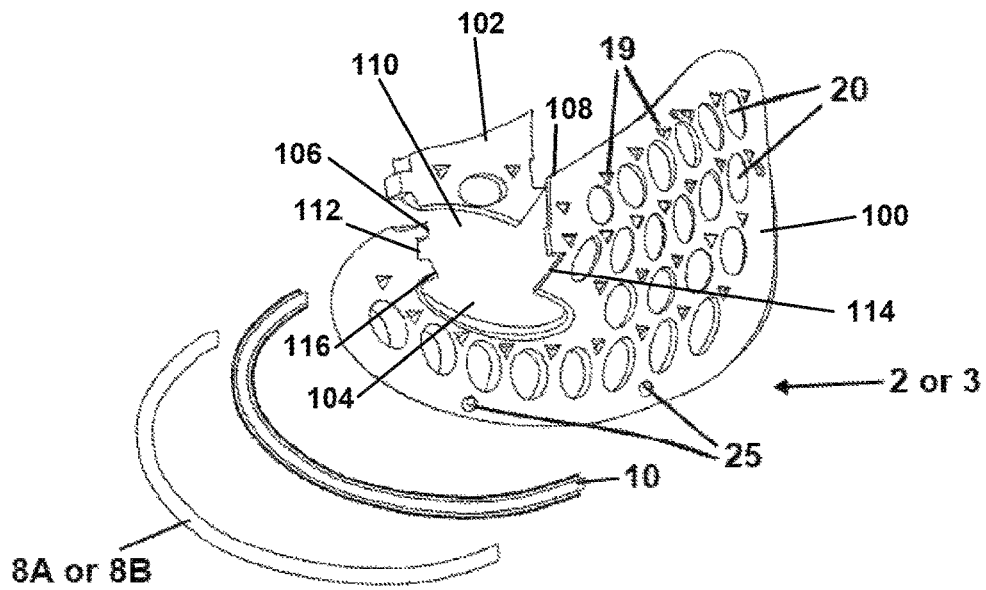
FIG. 5A is an exploded perspective view of a preferred embodiment of a femoral component of the prosthesis.
Figure 5B:
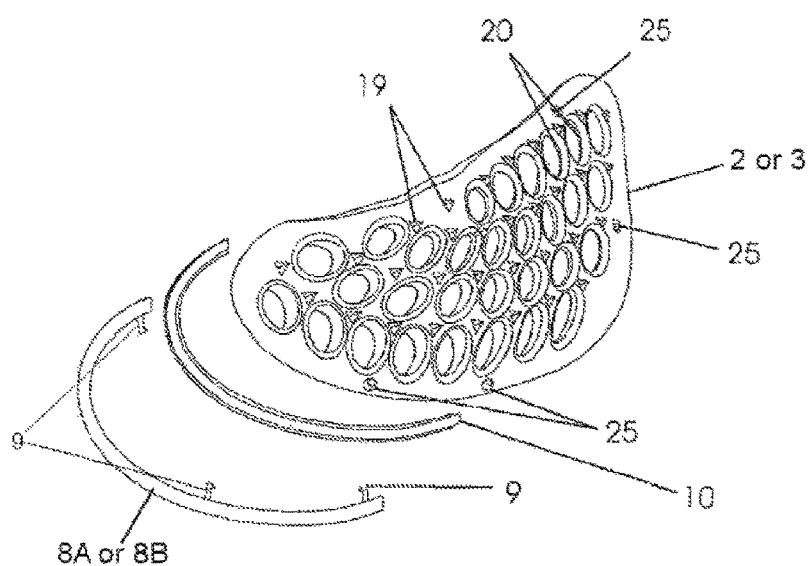
FIG. 5B is an exploded perspective view of an alternate embodiment of a femoral component of the prosthesis.

The articulating components 8A, 8B are attached to the femoral plates 2, 3 via fasteners. A first fastener embodiment is shown in FIG. 5A. An alternate embodiment fastener system is shown in FIG. 5B in which hooks 9 attach the articulating components 8A, 8B to the femoral components plates 2, 3.

The articulating surfaces of the articulating components 8A, 8B preferably have dimensions of approximately 2-3 mm thickness and approximately 4-6 mm of width. The length of the articulating surfaces can vary so as to fit different recipients. These are likely to be in the range of 12-18 mm.

The articulating surfaces of the invention are shaped to correspond to and/or mimic the articulating surface of the native femur bone forming part of the knee. The articulating surfaces do not have a simple mathematical shape. Rather, they are shaped and configured to mimic the function of and range of motion of, the native knee joint. This is important in the prosthesis providing a full range of motion being able to replace the knee joint rather than simply assist the native knee joint's operation.

It should also be noted that the articulating surfaces of the invention are positioned outside of the medial and lateral edges (respectively) of condoyles of the femur, as can be seen in FIG. 3, amongst others. Therefore, the articulating surfaces of the illustrated embodiment are not identical to the native articulating surfaces of the condoyles.

In a preferred embodiment, a deformable component 10 is provided in between the articulating components and the respective femoral plates 2, 3. Preferably the deformable component 10 is approximately 2-3 mm thick and is made of a bio-compatible polymer, and operates to absorb some of the forces applied through the joint. Preferably, the polymer has a young's modulus of approximately 5-20 times that of articular cartilage and is substantially impervious to creep. In a most preferred embodiment the polymers modulus is 5-10 times that of cartilage. It is also preferred that the material have a Poisson ratio of approximately 0.3 which is typical of cancellous bone. For example, the deformable member 10 may be a synthetic carbon polymer (eg: PMMA). Preferably, the deformable component 10 is made from a material which will allow the joint (as a whole) to deform in a manner comparable to normal articular cartilage under the expected physiological stress. It may be preferable that the deformable component deforms slightly less than typical cartilage in order to increase the proportion of the load transferred by the prosthesis.

Other materials suitable for the deformable component are Ultra High Molecular Weight Polyethylene (UHMWPE); silicone polycarbonate urethane; or rotaxane.

The deformable component 10, provides a deformable structure between the comparatively rigid femoral component 2, and corresponding tibial component 4, and bone. The component 10 is preferably held in place between the articulating component 8A or 8B and femoral plate 2.

The deformable component may be mated with the articulating component 8A or 8B and the respective femoral plate 2 or 3.

For instance, in the embodiment shown in FIG. 5A the femoral plates 2, 3 may include a groove 17 which receives a corresponding projection or rib of the deformable component 10. Similar grooves and projections may be provided at the interface between the component 10 and the articulating component 8A or 8B.

In one embodiment, the tibial plates are approximately 2-3 mm thick and approximately 4-6 mm wide.

Tibial articulating surfaces are provided on proximal margin of the tibial plates 4, 5. As shown in FIG. 3 amongst others, the articulating surfaces of the tibial plates 4, 5 are located outside of the lateral margins of the condoyles of the femur and tibia. Therefore, the articulating surfaces of the illustrated embodiment are not identical to the native articulating surfaces of the condoyles.

The tibial articulating surfaces are preferably shaped so as to correspond to and/or mimic approximately the middle two thirds of the medial/lateral border of the native knee joint articulating surface.

In one preferred embodiment, a separate articulating component may be secured to each of the tibial components 4, 5. Each articulating component has a shape that corresponds to the articulating surface of the native condoyles of the tibia. The articulating components are preferably a ceramic material secured to a metallic base. The ceramic material has a low coefficient of friction, therefore allowing the articulating surfaces of the femoral and tibial components to slide across each other with low or minimal resistance.

Figure 6B:
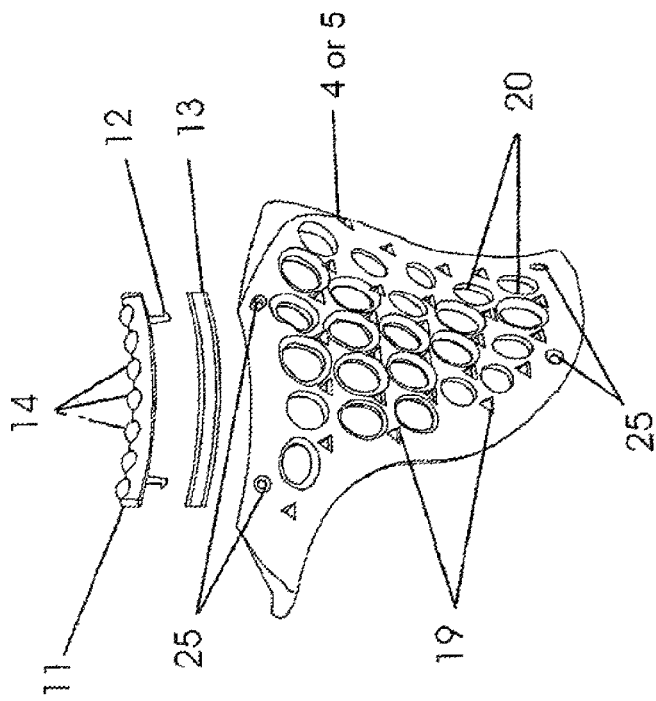
FIG. 6B is an exploded perspective view of an alternate embodiment of a tibial component of the prosthesis.

An alternative embodiment of an articulating surface is shown in FIG. 6B, where the articulating components 8A, 8B each include a plurality of ball bearings 14. Each ball bearing 14 is approximately 2 mm in diameter and made from ceramic coated stainless steel. There may be approximately 5 to 10 ball bearings 14, and the corresponding bearing housing may also be coated with a ceramic material to improve the wear characteristics of the interface. Alternatively, the tibial articulating components 8A, 8B may be a polished metal or ceramic surface.

The articulating components 8A, 8B act as an articulating surface that in use interacts with the corresponding articulating component on a femoral plate 2, 3, to provide a range of motion for the joint.

Figure 6A:
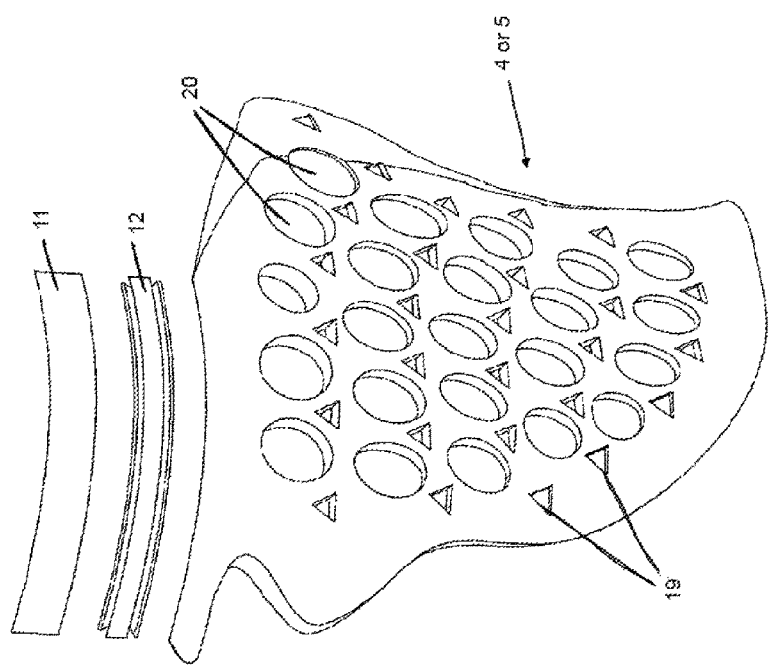
FIG. 6A is an exploded perspective view of a preferred embodiment of a tibial component of the prosthesis.
Figure 7:
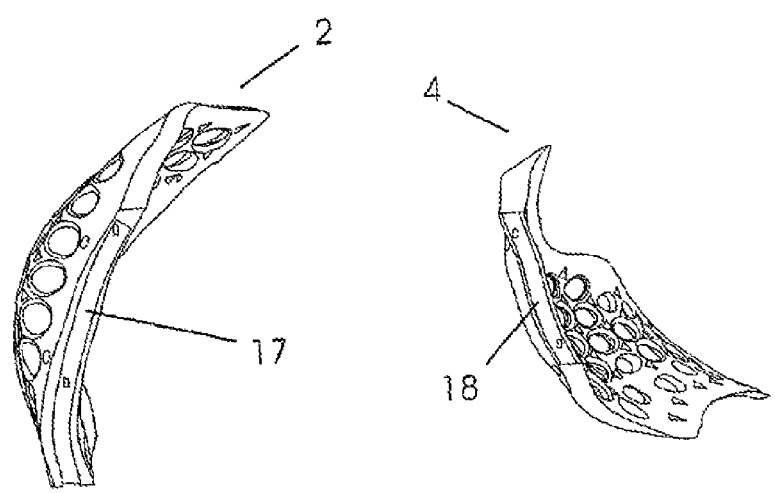
FIG. 7 is a view of a femoral component and a tibial component showing the mounting features.

The articulating components 8A, 8B can be secured to the tibial component using several fastener arrangements. For instance, one particularly preferred embodiment is shown in FIG. 6A, where a latch 11 mates with a corresponding groove (not shown) on tibial component 4, 5 to secure these together.

An alternate securing system is shown in FIG. 6B. A number of hooks 12 engage with apertures in tibial plate 4, 5.

A deformable component 13 may be provided between the articulating components, and the tibial plate 4, 5. The deformable component 13 is approximately 2-3 mm thick. To secure the deformable component 13, between the articulating components and the tibial components, the underside 17 of articulating component 8A, 8B may have a longitudinal groove (shown in FIG. 7) for receiving and mating with the deformable component 13. Similarly, the deformable component 13 may have a rib or projection on the underside for a corresponding groove 18 in the proximal edge of the tibial plates 4, 5.

In their preferred forms, the femoral plates 2, 3 and tibial plates 4, 5 are made from a non-bioactive material that is stiff and hard such as stainless steel or titanium. In a most preferred form, titanium is used. It is also preferred that both the femoral and tibial plates include a number of apertures or holes 20. This reduces the bulk of the metal without significantly compromising its stress distributing properties. The holes may also allow soft tissue attachment and hence the nutrition of the bone thereby not disturbing normal biology significantly.

The superficial surface of the femoral and tibial plates 2-5 are preferably polished to minimize rubbing of the surrounding soft tissues which may result in irritation. The deep surfaces are also smooth, but may include multiple protrusions (not shown) to keep the component distanced from the bone surface. For example, a number of spaced protrusions approximately 1 mm long may project from the deep surfaces, to separate the plates from the bone, in order to reduce the risk of pressure necrosis of the bone commonly seen after plating of fractured bone.

The prosthesis according to the present invention is a stress sharing device suitable for minimally invasive, surgical implantation around the knee joint without compromising the native joint surface. Accordingly, it substantively transfers potentially damaging stress from the joint and distributes this to the tibia and femur bones at locations away from the joint. This allows the joint to repair itself by maintaining the basic physiological strain at the joint surface. In extreme cases the prosthesis could take substantially all the stress from the joint. The articulating surfaces facilitate the joint having a desired range of motion.

The present invention may also find application as a stabilisation method for treatment of intra-articular fractures.

Multi-Component Plates

Referring now to FIG. 5A. The femoral plate 2 may be provided by a first component 100 and a second component 102. The first component 100 has an aperture 104 which extends from the deep surface to the superficial surface of the femoral plate 2. The aperture 104 is open at an edge 106 to the perimeter 108 of the plate 2, which defines a channel indicated as 110. The channel 110 includes a generally square shaped sub-channel 112, a generally triangular shaped sub-channel 114, and a generally square shaped protrusion 116.

The second component 102 has a shape corresponding to the shape of the channel 110. In addition, the second component 102 has structure 118, 120, 122 configured to engage with the structure 112, 114, 116 in the first component 100.

The aperture 104 has a generally oval shape and is configured to receive the deep medial collateral ligament 150 and the medial collateral ligament 152, as can be seen in FIGS. 20D and 23A-D.

While not shown in FIG. 5A, the femoral plate 3, has a similar two-part structure to the femoral plate 2.

Provision of an aperture in a plate 2 or 3 of the invention may facilitate provision of a knee implant with minimal damage, irritation or disturbance to the native soft tissue of the joint. For instance, the aperture enables the plate(s) to accommodate the native ligaments. The prosthesis according to the invention can also therefore use the native ligaments to achieve movement of the bones of the joint.

Fastening Methods

In one preferred form, the tibial and femoral plates 2-5, have multiple triangular holes 19 to accommodate corresponding bone fasteners 15. Preferably, the flat portion of the triangle shaped holes 19 is oriented to be perpendicular to the line of stress through the joint, to improve transmission of stress from the prosthesis to the bone. That is, the points of the triangle are oriented to point towards the respective joint surface. As best shown in FIG. 3, the triangle points face downwards for the femoral plates 2, 3, and triangle points face upwards for the tibial plates 4, 5.

The bone fastener pins 15 are designed to transmit the stress from the femoral and tibial plates to the corresponding bony structures to which they are attached. The fastener 15 is hammered into the bone through the apertures 19 in the femoral and tibial plates.

One embodiment of a fastener is shown in FIG. 8A. One end of the fastener 15 includes a head 21, having a triangular cross section. The head 21 narrows through body section 22 to point 23. End 21 has an engagement point 22 and a plurality of barbs 16 extend from body section.

In use, fastener pins 15 are inserted through holes 19 in the plates 2-5 further than required. Engagement point 22 is used to draw the fastener pin 15 backwards towards femoral and tibial plates 2-5. This assists in barbs 16 engaging the cancellous bone so as to secure the fastener pins 15, and thereby the plates 2-5, in position.

An alternate embodiment of the fastener pin is shown in FIG. 8B. End 21 has a thin sheet of elastic metal 24 attached at the center. Elastic metal sheet 24 is larger in size as compared to end 21. During insertion, end 21 should be pushed in further to preload the fasteners pins in their inserted position. This will create elastic recoil and help to fix the barb end in the cancellous bone. The point end 23, preferably includes a barb 16 for fixation in the cancellous bone. In its preferred form, the barb 16 is approximately 5 mm in length.

The bone fastener may be made from stainless steel, or most preferably, titanium.

Figure 4:
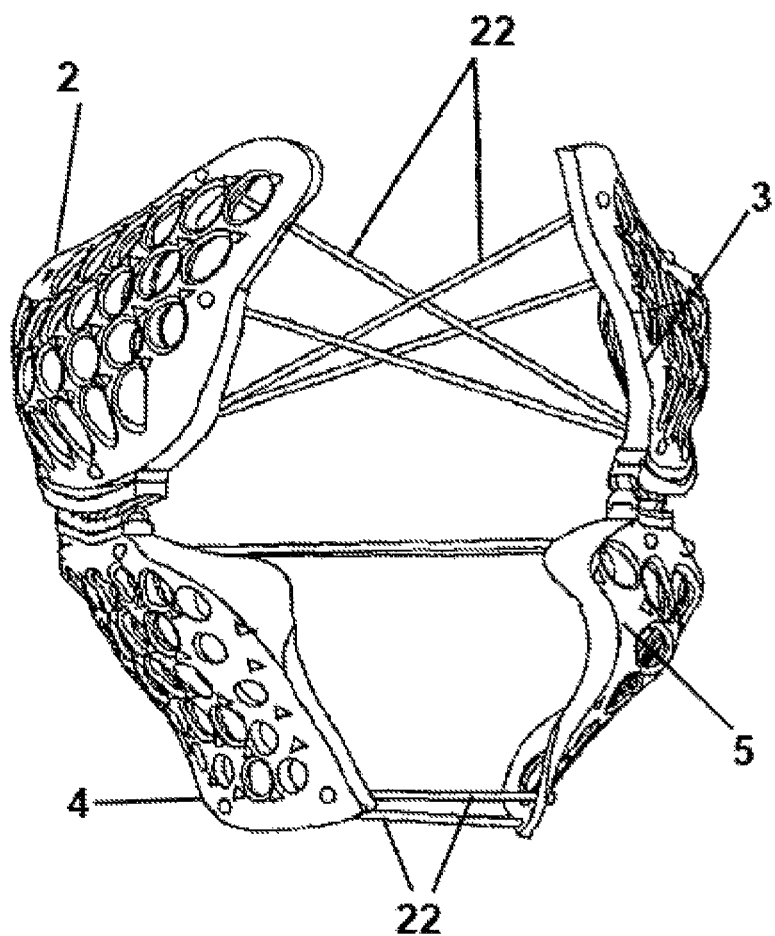
FIG. 4 is a rear perspective view of the prosthesis shown without the joint.

The medial and lateral femoral plates 2, 3 may also be fixed with a number of locking rods 22 as shown in FIGS. 3 & 4. These four locking rods 22 pass through the corresponding bone are fix the pair of femoral plates and tibial plates together respectively. The plates 2-5 also have holes for the attachment of the cross rods 22. In order to insert the rods 22, a hole is drilled in the bone to accommodate the rods. A guide is used to direct the drill hole between the corresponding holes 25 in the femoral/tibial plate. The required length of the rods 22 are measured by the guide. A ball tipped rod 22 is inserted from one side, while the other end of the rod 22 is threaded. A nut is applied to the threaded end, and tightened to achieve the required strain. The excess thread can then be cut flush.

Alternatively, it is envisaged that conventional screwing techniques could also be used to fix the prosthesis to the bony structures.

Implantation Method

A method is provided for implantation of the prosthesis according to the present invention. The method will be described herein with reference to insertion of the knee joint. However this should not be seen as limiting and it should be appreciated that similar steps are involved in implanting prosthesis to other joints. One skilled in the art should be able to extrapolate from the steps described herein so as to work the present invention.

Before implanting the prosthesis, the patient's knee joint may be examined by a non-invasive imaging procedure such that appropriately sized and shaped components may be selected. A variety of non-invasive imaging devices may be suitable, for example CT scan, or X-ray devices and the like. Two methods of non-invasive imaging for selection of a suitable prosthesis are preferred.

In the first method, CT scan or other non-invasive imaging scans, optionally coupled with exterior measurements of the dimensions of the relevant proximal tibia and proximal femur bone, may be used to establish a library of prostheses whose size and geometry differ according size of the patient. A limited number of "standard" prostheses are then made to meet the requirements of a generic population of patients. In this first method, a non-invasive imaging scan, such as an X-ray or CT scan, together with clinical measurement will enable the surgeon to select a prosthesis of the best size and shape from the library for a particular patient. With this method, it is expected that some modification of the patient's bony structure may be necessary. However, an extensive set of standard sizes can be created to minimize the modification required to the joint's anatomy.

In a second method, each patient receives one or more prostheses that are custom tailored for the individual. Such a prosthesis may be constructed from imaging data (i.e., X-ray or CT scan data) by a suitable computer program. The second method is likely to result in an improved fit to a patient's unique anatomy, and/or reduce the need to shape the exterior surfaces of the patient's bones.

Surgery can be done under general or local anesthesia. The patient is positioned supine with a radiolucent wedge located underneath the knee, and the operation is done under tourniquet control and image intensifier guidance. An antero-lateral and posteromedial approach to the distal femur and proximal tibia is utilized to approach the distal femur and proximal femur. All the soft tissue is taken off from the bone as a soft tissue sleeve.

Insertion of the prosthesis of the present invention is typically done via a 10 cm to 14 cm length incision to the capsule on the medial and lateral margins of the joint. The articulating body of the femoral component is aligned with the lateral/medial edge of joint surface. Its position is checked visually and radiological using intra-operative X-ray. Once acceptable alignment is achieved, it is temporarily fixed with the help of wires. A set of standard size templates may be provided during the surgery to achieve initial alignment and appropriate sizing. Once an exact size is determined the prosthesis is applied using the initial temporary wires. All other components of the prosthesis are attached on this base line.

The tibial component engages with femoral articulating body and it can be preloaded depending on the clinical requirement. A pre-compression of the polymer insert 10 can function to take the resting stress from the joint surface.

The next step of implantation is to align an appropriately sized articulating body of the femur with the joint surface and the lateral/medial edge of the femoral condyle. The implant should correspond to the condylar line in a lateral knee X-ray. Next, the tibial articulating body is placed opposing the femoral plate. Both plates are temporarily fixed with K-wires. The appropriate position and size can be checked using an image intensifier and an AP view is taken to check the joint space. A pre-stress device can be used to pre-stress the implant according to clinical requirement by compressing the deformable component. Once in the correct position, rods 22 are used to fix the plates, and the triangular fasteners are hammered into the bone. The temporary K-wires are then removed. The joint can then be tested and taken through the full range of motion.

Referring now to FIGS. 20A-D which show a medial side view of the steps of positioning a femoral plate 2 relative to the condoyle of the femur. The steps generally form part of the method of implanting the prosthesis as described above and may therefore be used in combination with the same, or in combination with other steps/methods.

An incision is made to the layers of the capsule as noted above. The ligament(s) of the joint are separated from the membrane forming the outer layer of the capsule.

The first component 100 is inserted through the insertion and positioned adjacent the medial condoyle of the femur. A perimeter side of femoral plate 2 is slid under the medial collateral ligament 152 and the deep medial collateral ligament 152 so that these ligaments are positioned in the channel 110.

Figure 20A:
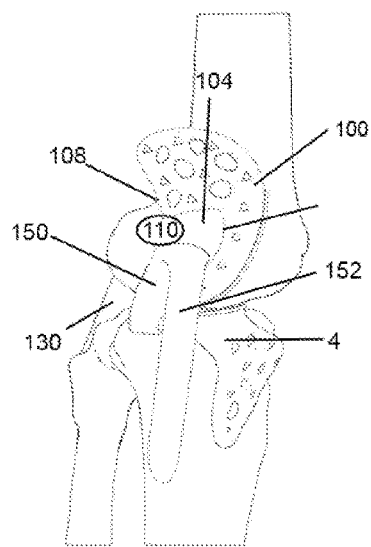
FIGS. 20A-D are side views of a knee showing representative steps in fitting a prosthesis according to the present invention.
Figure 20B:
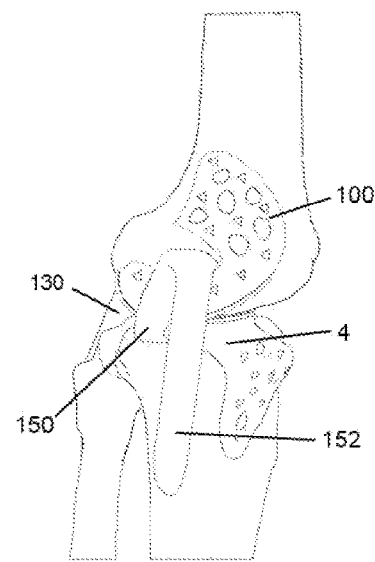
Figure 20C:
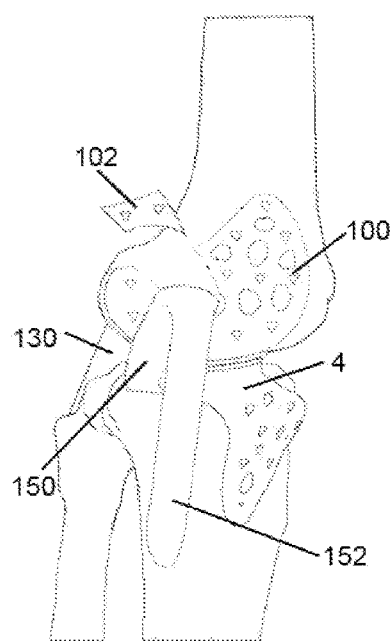

The first component 100 is rotated so that the ligaments are moved into the aperture 110 to the position shown in FIG. 20B. Rotation of the first component 100 continues until it reaches the position shown in FIG. 20C.

Figure 20D:
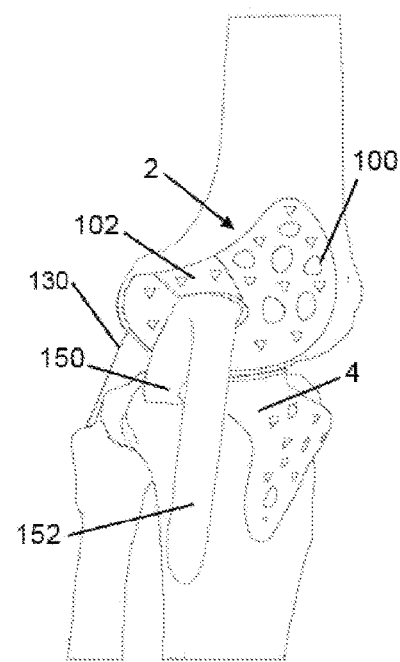
Figure 23A:
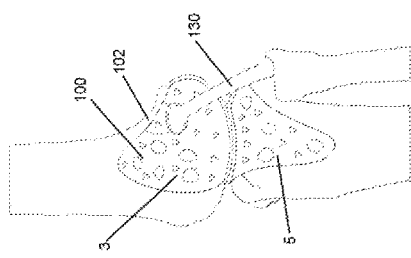
Figure 23B:
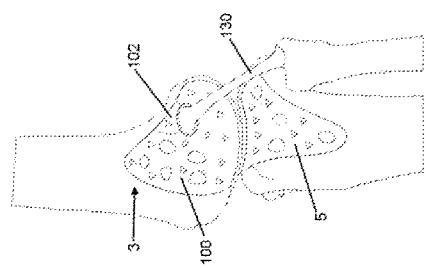
Figure 22A:
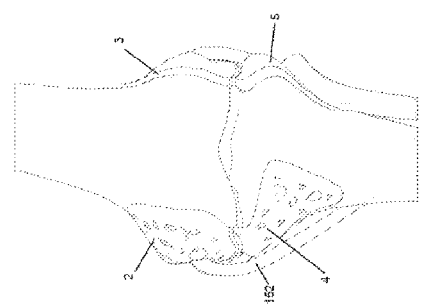
FIGS. 22A-E are anterior views of a patient's left knee showing a prosthesis according to the present invention facilitating movement between extension and flexion.
Figure 22B:
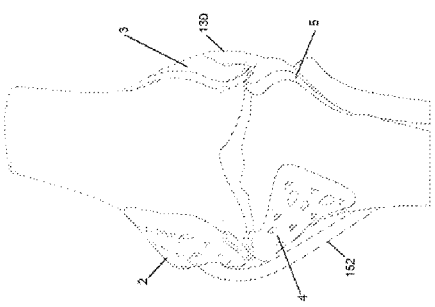
Figure 21A:
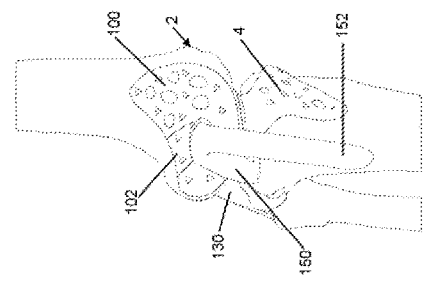
FIGS. 21A-E are medial views of a patient's left knee showing a prosthesis according to the present invention facilitating movement between extension and flexion.
Figure 21B:
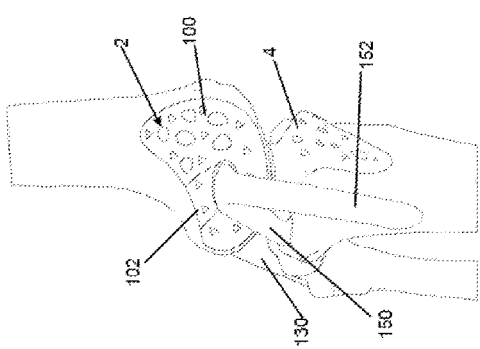
Figure 23C:
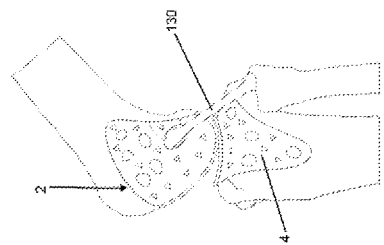
Figure 23D:
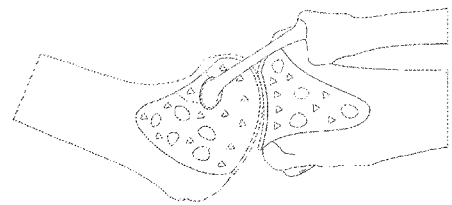
Figure 22C:
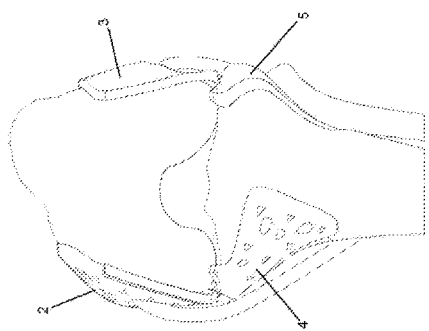
Figure 22D:
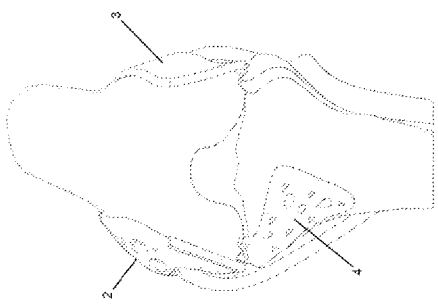
Figure 21C:
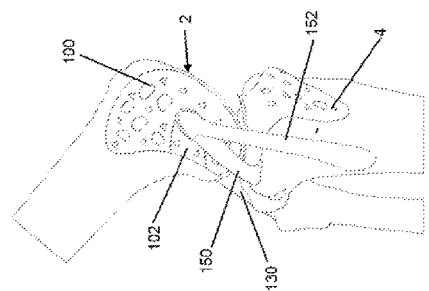
Figure 21D:
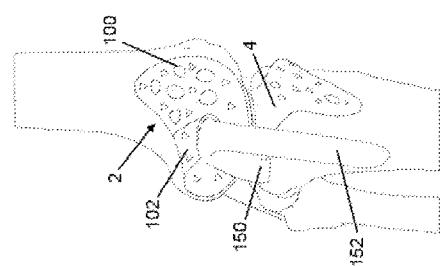
Figure 23E:
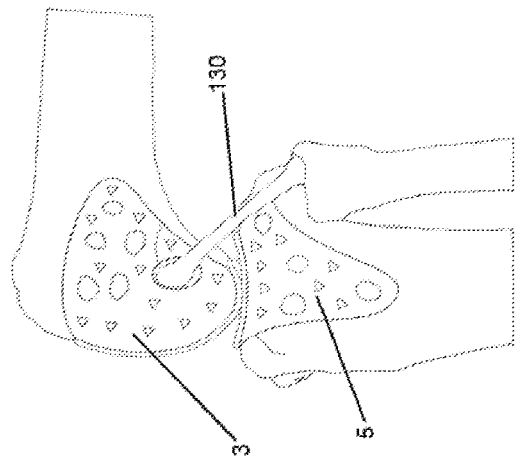
Figure 22E:
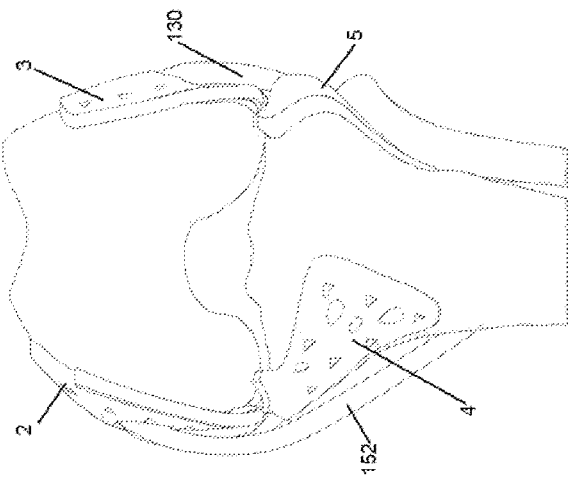
Figure 21E:
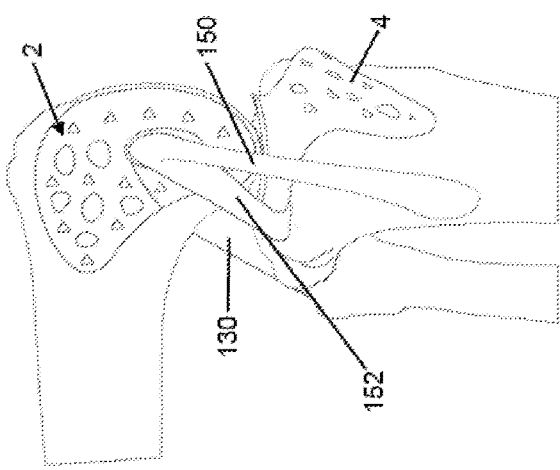

The second component 102 is positioned relative to the first component 100 and inserted into the channel 110 as is shown in FIG. 20D. The structures on the first and second components 100, 102 engage each other.

A similar process can be used to position the deep lateral collateral ligament (not shown in FIGS. 20A-20D) and lateral collateral ligament 132 in a corresponding aperture 130 in femoral plate 3, to assume the position shown in FIGS. 23A-E.

Figure 27:
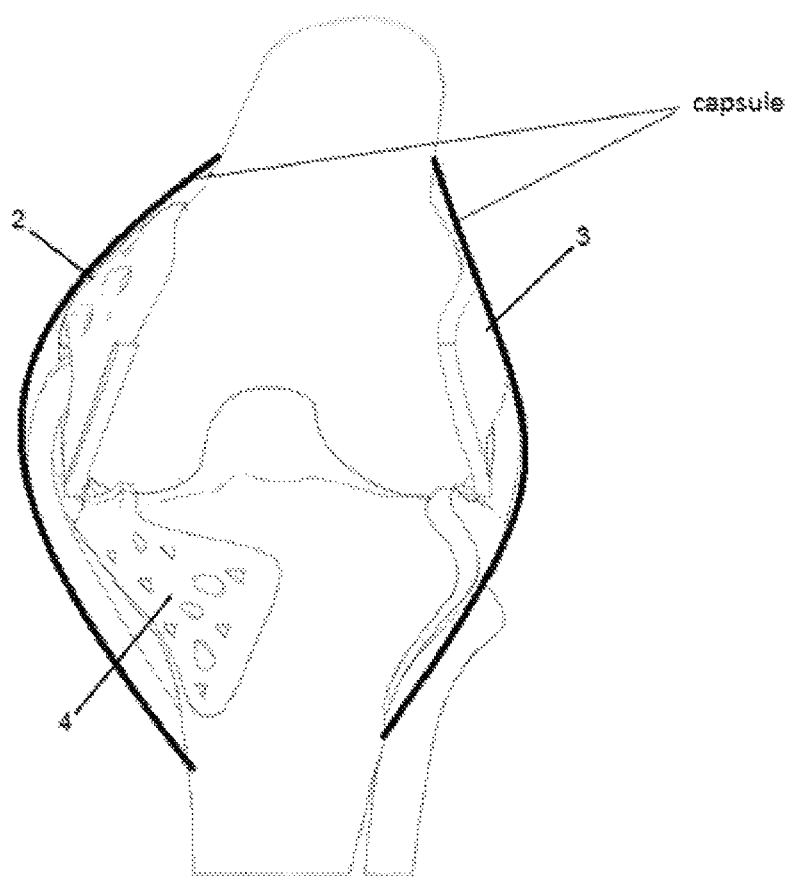
FIG. 27 is an anterior view of a knee joint showing a knee prosthesis according to an embodiment of the invention and the capsule.

The components of a prosthesis of the invention are located inside the capsule, and therefore the invention provides an inter-joint prosthesis. FIG. 27 shows the location of the prosthesis relative to the native knee joint and in particular the capsule 160. As can been seen, the ligaments 132, 150 have been separated from the outer membrane forming part of the knee joint and the plates 2, 3, 4, 5 are positioned to accommodate the ligaments 132, 150.

Alternative Plate Configurations

Referring now to FIGS. 24 to 26 which show alternative embodiments for a two part femoral plate 2 or 3 according to an aspect of the invention. The embodiments of FIGS. 24 to 26 differ in the shapes of the respective components from which they are formed as illustrated.

Figure 24A:
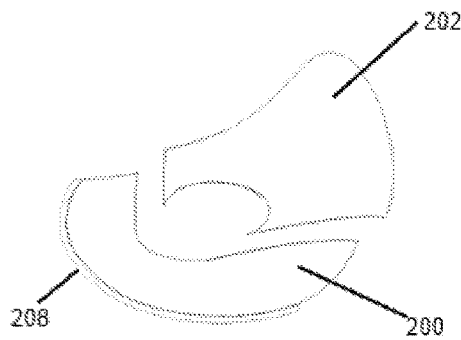
FIG. 24A is a side exploded view of an alternate embodiment of a femoral plate according to an embodiment of the invention.
Figure 24B:
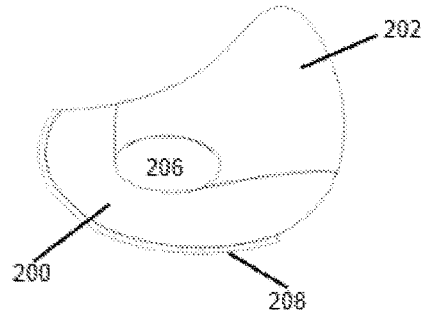
FIG. 24B is a side view showing the femoral plate of FIG. 24A assembled.

FIGS. 24A and 24B show that the first component 200 and the second component 202 together provide a generally tear shaped femoral plate having an aperture 206 to in use accommodate the native ligaments in the knee.

An articulating surface 208 is provided on the first component 200, and is configured to in use cooperate with a corresponding articulating surface on a tibial plate.

Figure 25A:
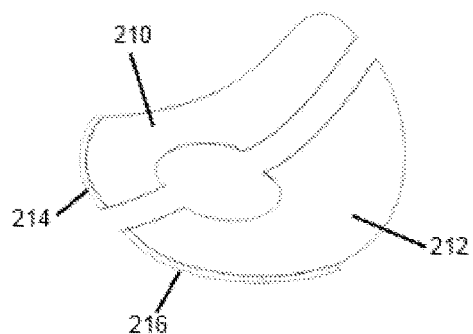
FIG. 25A is a side exploded view of a second alternate embodiment of a femoral plate according to an embodiment of the invention.
Figure 25B:
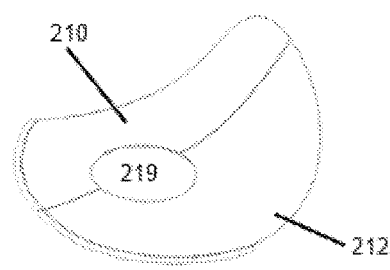
FIG. 25B is a side view showing the femoral plate of FIG. 25A assembled.

FIGS. 25A and 25B show a first component 210 and a second component 212. A first articulating surface 214 and a second articulating 216 surface are provided on the first component 210 and the second component respectively. In use, the first and second articulating surfaces 214, 216 together provide an articulating surface for the femoral plate.

Together the first component 218 and the second component 220 define an aperture 225 to in use accommodate the native ligaments in the knee.

Figure 26A:
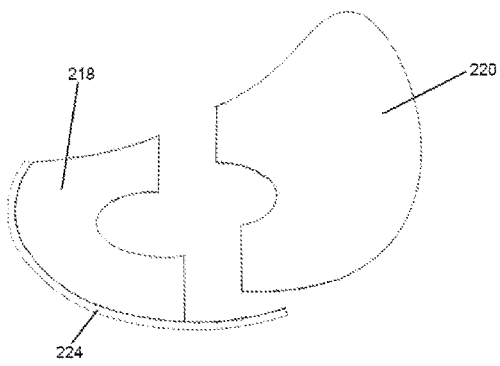
FIG. 26A is a side exploded view of a third alternate embodiment of a femoral plate according to an embodiment of the invention.
Figure 26B:
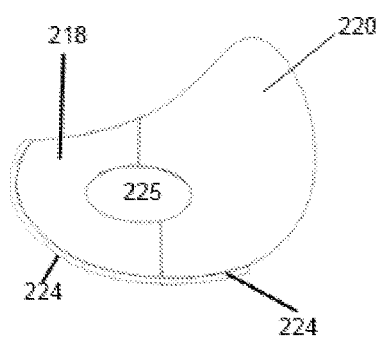
FIG. 26B is a side view showing the femoral plate of FIG. 26A assembled.

Similarly, FIGS. 26A and 26B show a first component 218 and a second component 220. The entire articulating surface (224) is provided on the first component 218 in FIGS. 26A and 26B.

While the embodiments of FIGS. 24 to 26 all include a generally oval shaped aperture, this should not be seen as limiting. For instance, the aperture may be round or spiral shaped, or have any other appropriate shape. In addition, while the shape of the combined first and second components is generally tear shaped, other shapes are also envisaged.

Range of Motion

Referring now to FIGS. 21A to 21E, 22A to 22E and 23A to 23E.

The pair of medial plates cooperate with each other and the pair of lateral plates cooperate with each other, to guide the bones of the knee joint through a desired range of motion. As can be seen, the native ligaments are accommodated by the plates as they can extend through the apertures therein. This enables the native ligaments to hold the bones of the joint (and therefore the plates attached thereto) together. Muscles can therefore move the knee joint. Because the plates accommodate the native ligaments the function of the native knee joint is substantially unaffected by the prosthesis. In addition, the shape and configuration (as described above) reduces irritation or adverse effects of the plates on the ligaments of the joint.

In addition, the articulating surfaces of the plates provide a desired range of motion such as a required functional range of motion or a range of motion otherwise corresponding to the range of motion of the native knee joint.

Elbow Prosthesis

Figure 10:
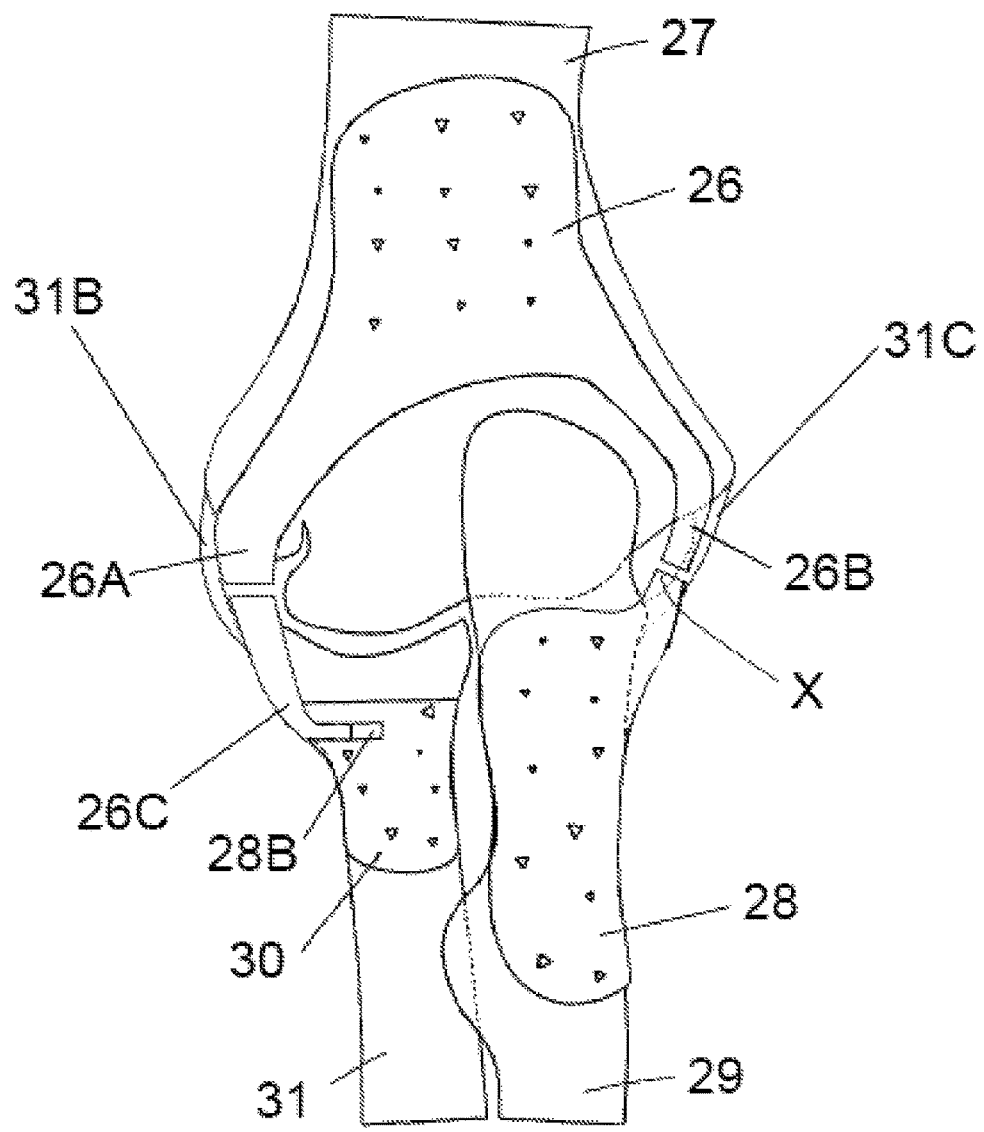
FIG. 10 is a front view of an elbow in extension with a prosthesis according to the present invention.
Figure 11:
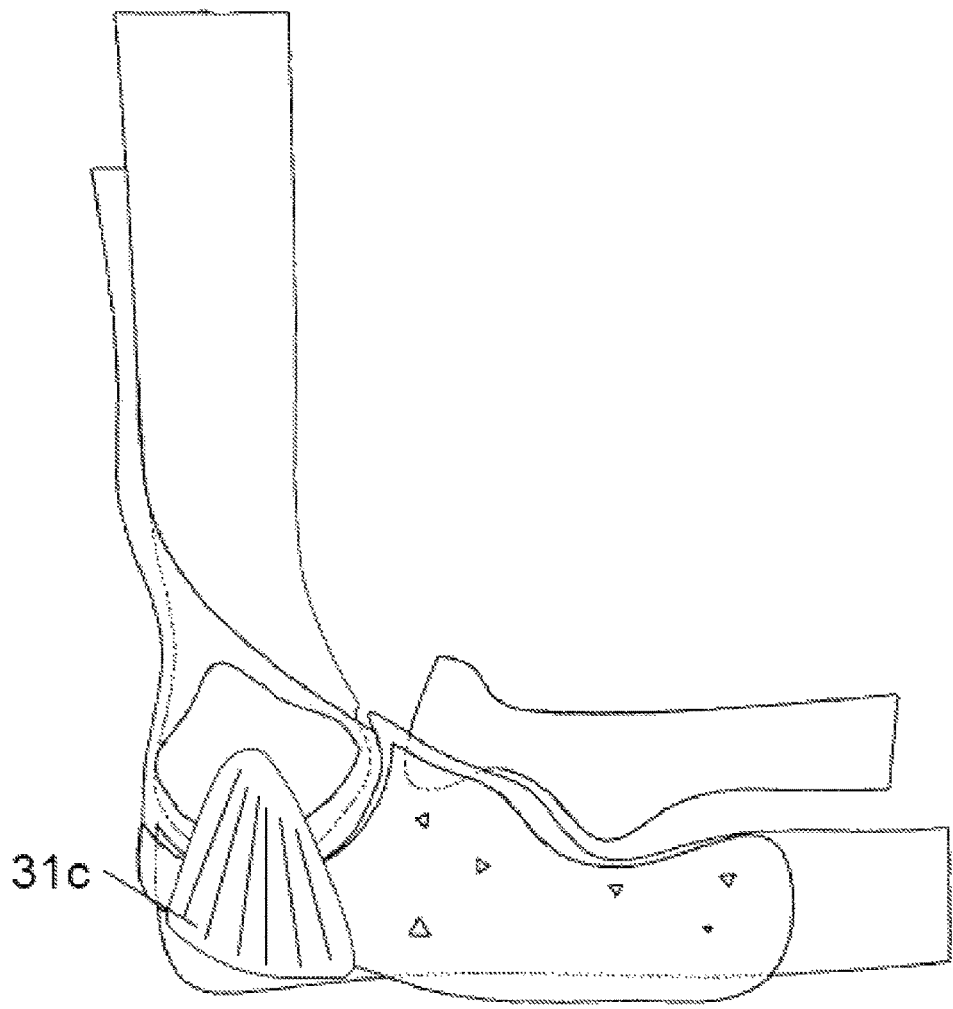
FIG. 11 is a side view of an elbow in flexion with a prosthesis according to the present invention.

Referring now to FIGS. 10 and 11 showing an elbow having a prosthesis according to the present invention in extension and flexion.

A first plate 26 is secured to distal end of humerus 27. The first plate has a generally "Y" shape with first arm 26A and second arm 26B. The arms diverge so as to surround the condyle of humerus 27.

A protrusion 26C provides an articulating surface between first plate 26 and third plate. A second plate 28 is secured to proximal end of ulna 29 and a third plate 30 is secured to proximal end of radius 31.

Arm 26B provides a articulating surface that cooperates with bearing surface on second plate (indicated generally as X) so as to facilitate the ulna moving with respect to the humerus and to provide for flexion and extension of the elbow joint. This is achieved by the articulating surfaces being shaped so as to correspond to and/or mimic the articulating surfaces of a native elbow joint responsible for flexion and extension.

Protrusion 26C acts as another articulating surface by slidingly cooperating with groove 30B in the third plate. The protrusion 26C can slide across arm 26A. This provides rotational motion of the radius with respect to the humerus. That is, cooperation between articulating surfaces on the first and third plates facilitates pronation and supination of the radius 31.

As can be seen in the FIGS. 10 and 11, the first plate, second plate and third plate accommodate the native ligaments of the elbow joint, being the lateral collateral ligament 31B and the medial collateral ligament 31C. Accordingly, the ligaments 31B, 31C can hold the joints of the bone in position as in an untreated joint.

Ankle Prosthesis

Figure 18:
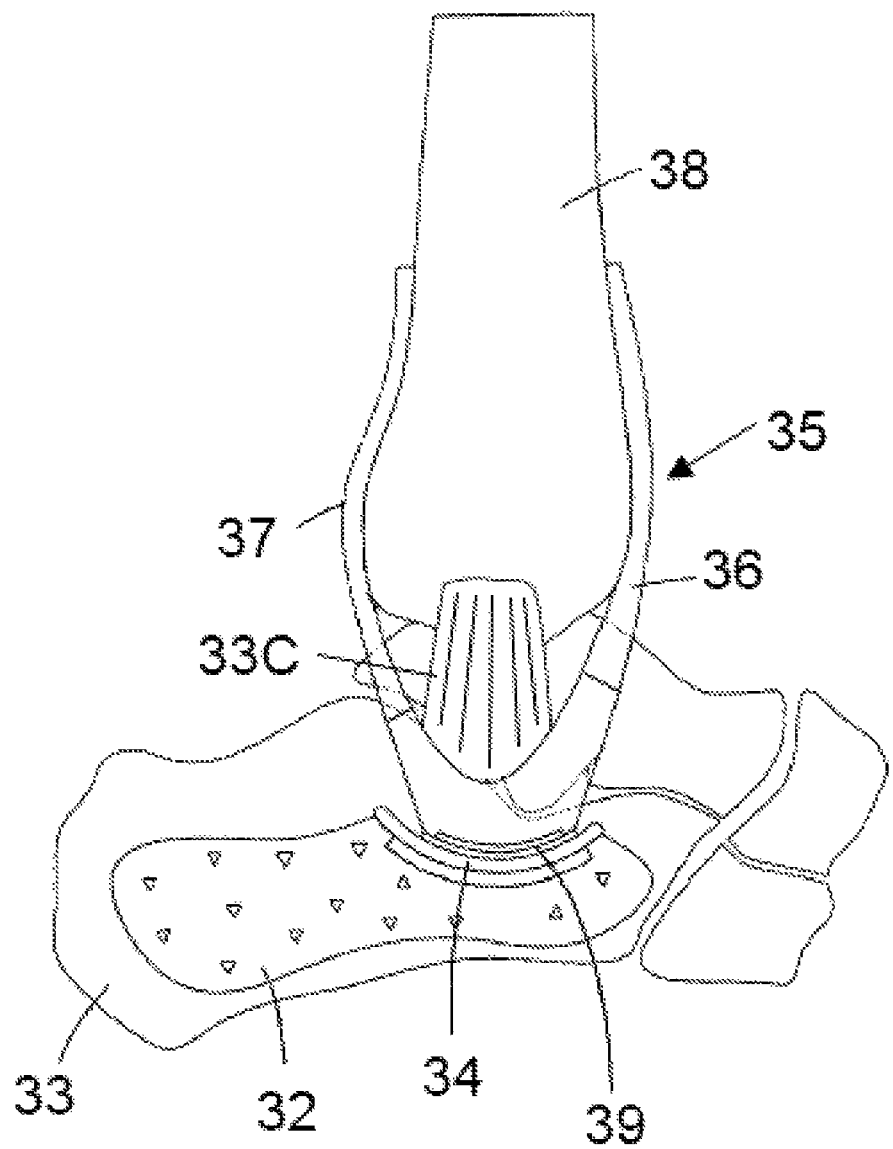
FIG. 18 is a side view of an ankle including a prosthesis according to the present invention.
Figure 19:
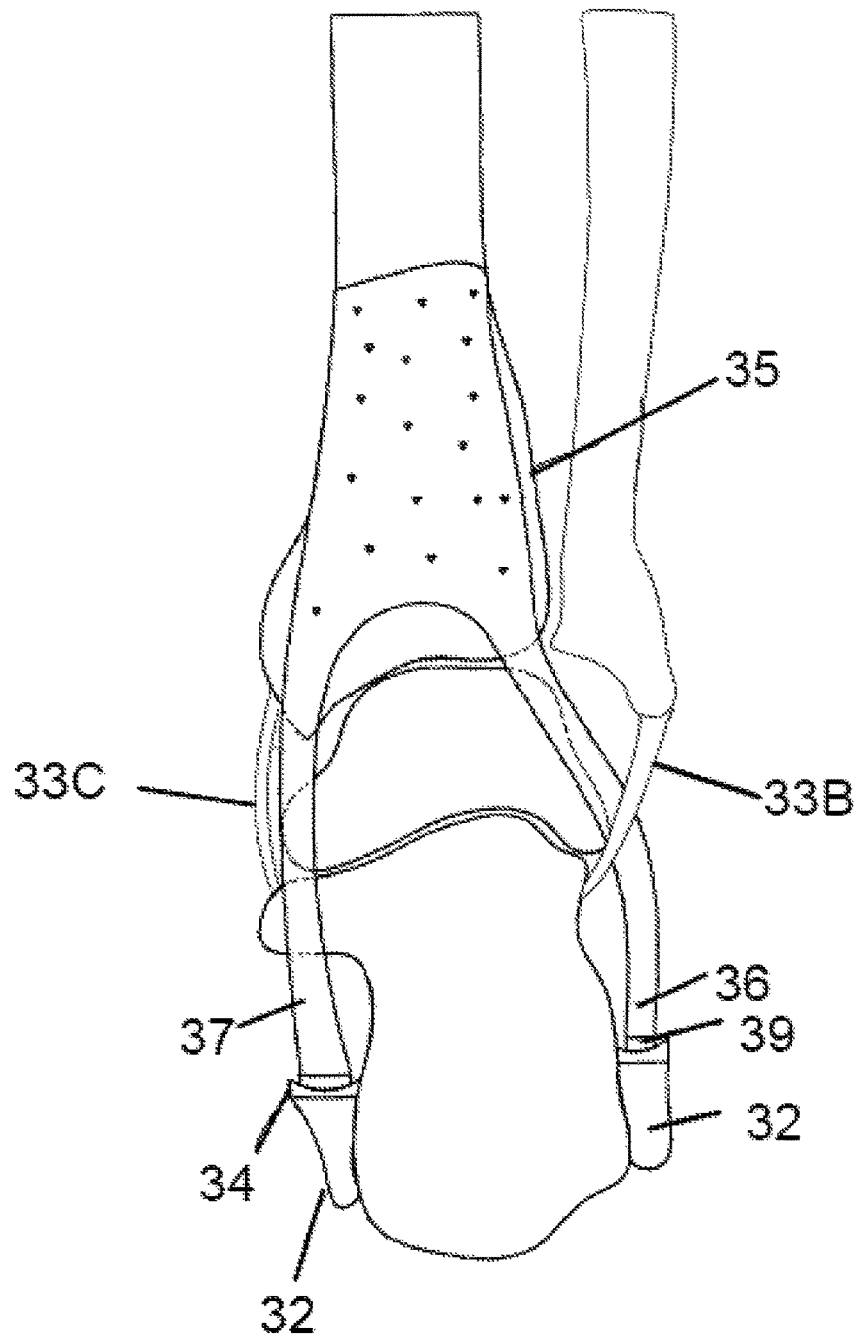
FIG. 19 is a back view of FIG. 18.

Referring now to FIGS. 18 and 19 which show an ankle prosthesis is configured to replicate motion of the native ankle joint. The configuration of the prosthesis is designed to enable insertion into the restricted space of the ankle joint. This is necessary as the configuration of a foot and ankle joint means that there is little room to secure components of the prosthesis.

A first plate 32 having an articulating surface 33 is secured to calcaneum bone 34 on the lateral/medial edge of a foot. Articulating surface 33 has a generally concave shape when viewed from the lateral edge of the foot.

A second plate 35 has first arm 36 and second arm 37. The arms 36, 37 diverge so as to be able to surround front and back edges of tibia 38. The arms provide articulating surfaces 39 which are generally convex in shape when viewed from the lateral edge of the foot.

Articulating surfaces 33, 39 are arcs of a circle. Therefore, the articulating surfaces define a range of motion similar to the native ankle joint. However, bearing surfaces 33, 39 are not shaped to correspond to the native ankle joint articulating surface.

Articulating surface 33 is slightly wider laterally than articulating surface 39. This allows for the lateral movement of the foot.

As can be seen in the FIGS. 18 and 19, the first plate and second plate and third plate accommodate the native ligaments of the ankle joint, being the lateral collateral ligament 33B and the medial collateral ligament 313. Accordingly, the ligaments 33B, 33C can hold the joints of the bone in position as in an untreated joint.

Finger Prosthesis

Figure 12:
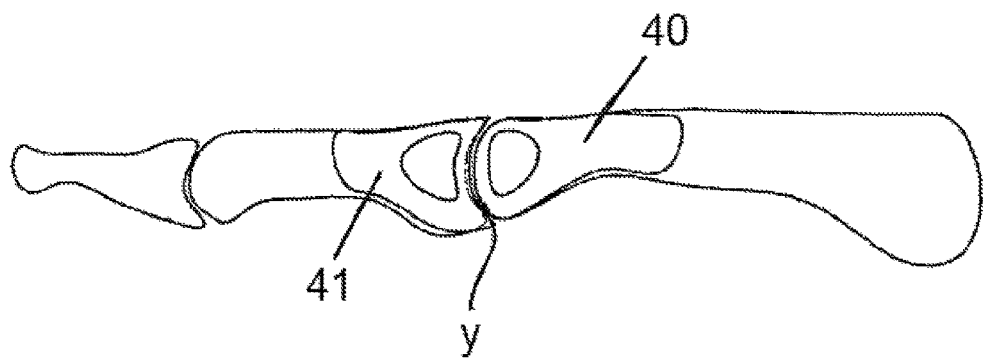
FIG. 12 is a side view of a finger in extension with the prosthesis according to the present invention.
Figure 13:
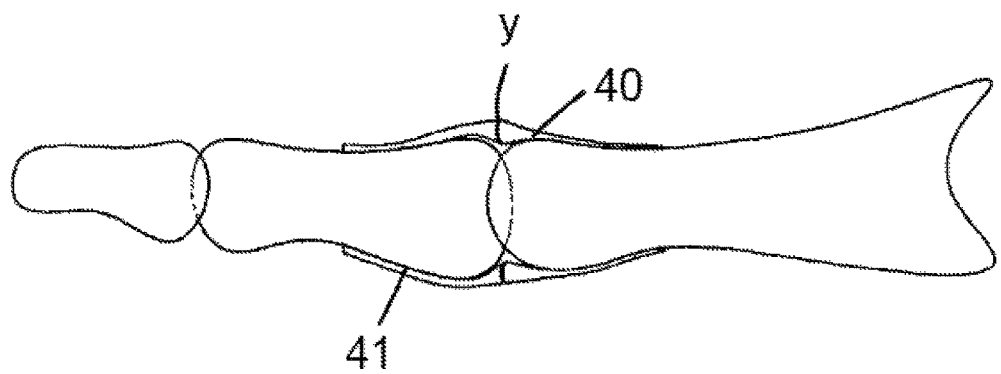
FIG. 13 is a front view of FIG. 12.

Referring now to FIGS. 12 and 13 that show a finger prosthesis according to the present invention.

A first plate 40 is attached to a distal portion of a bone forming part of a joint, and a second plate 41 is attached to a proximal part of a bone forming part of the joint. The first and second plates 40, 41 have bearing surfaces (indicated generally by Y) that cooperate to guide the second bone through a desired range of motion.

It is possible to have pairs of plates on distal sides of a joint as can be seen in FIG. 13.

The shape and configuration of the plates and their respective articulating surfaces will vary according to the finger joint within which the prosthesis is used. For instance, different shapes and ranges of motion are needed in a finger joint between a metacarpal and a proximal phalanges, compared to a finger joint between proximal phalanx and middle phalanx.

As with other embodiments, the prosthesis guides the bones forming the joint through a range of motion and acts as a surface for that motion to occur.

Deformable components may or may not be used with a prosthesis for a finger joint as these do not experience the same stresses as do load bearing joints such as the knee or ankle.

As can be seen in the FIGS. 10 and 11, the first plate, second plate and third plate accommodate the native ligaments of the elbow joint, being the lateral collateral ligament 31B and the medial collateral ligament 31C. Accordingly, the ligaments 31B, 31C can hold the joints of the bone in position as in an untreated joint.

Hip Prosthesis

Figure 14:
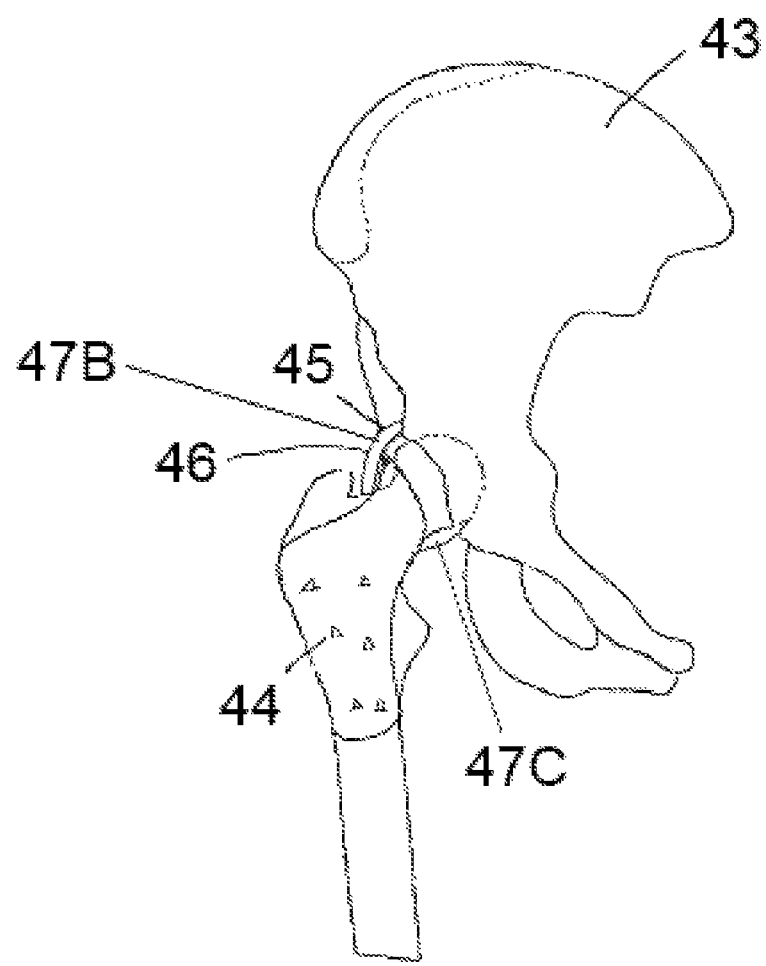
FIG. 14 is a front view of a hip joint with a prosthesis according to the present invention.
Figure 15:
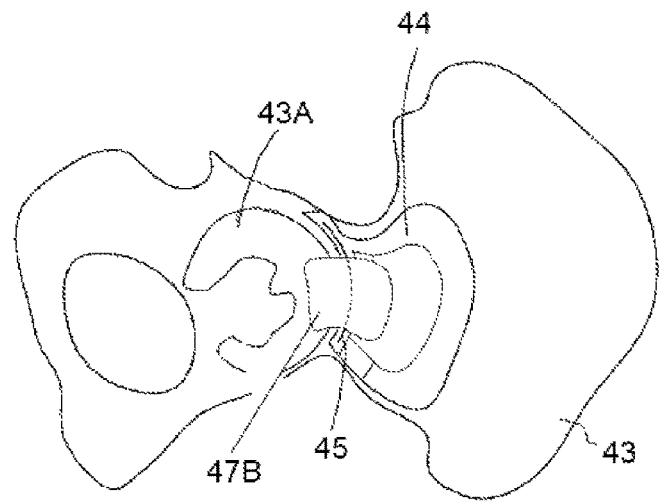
FIG. 15 is a partial view of a pelvis showing components of a prosthesis according to the present invention.

Referring now to FIGS. 14 and 15 which show a hip prosthesis according to an embodiment of the invention. The hip prosthesis includes a first plate 42 secured to pelvis 43 near acetabulum 43A. First plate 42 has an articulating surface in the form of a socket having a curve. The socket has a lip which extends away from the pelvis so as to define a cavity to receive a corresponding articulating surface 45.

A second plate 44 is secured to proximal end of femur. Second plate has an articulating surface 45 with the same curvature as that of first plate's articulating surface 46. However articulating surface 45 is smaller than articulating surface 46. This will allow articulating surfaces 45, 46 to move with respect to each other, and therefore provide a range of motion for the hip joint.

Articulating surface 46 extends over the edge between the native femur and acetabulum so as to engage with articulating surface 45.

The radius of curvature of the articulating surfaces 45, 46 is greater than the radius of curvature of the articulating surfaces in the native hip joint. This may assist in keeping the native joints separated from each other.

The articulating surfaces 45, 46 guide the femur bone and facilitate this moving with respect to the hip joint. The components maintain separation between the bones of the hip joint and provide a surface for relative movement of these.

A deformable component (not visible) can be used between the first and second plates. This allows forces applied to the joint to be transferred into the cartilage of the joint. However the deformable component is configured to maintain separation of the hip bones, so that movement of the femur with respect to the pelvis occurs via the bearing surfaces.

As can be seen in the FIGS. 14 and 15, the first plate and the second plate accommodate the native ligaments of the hip joint, being the illiofemoral ligament 47B and the pubofemoral ligament 47C. Accordingly, the ligaments 47B, 47C can hold the joints of the bone in position as in an untreated joint.

Shoulder Prosthesis

Figure 16:
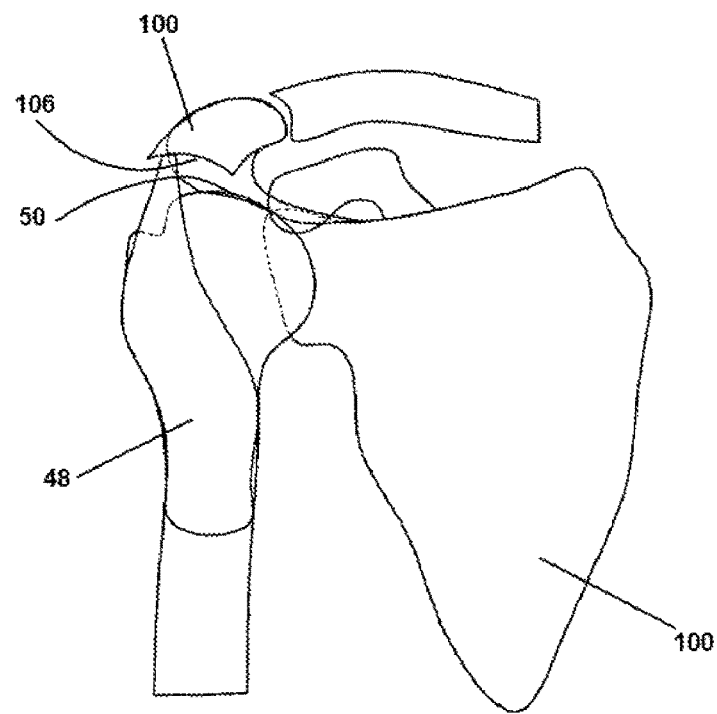
FIG. 16 is a front view of a shoulder joint including a prosthesis according to the present invention.
Figure 17:
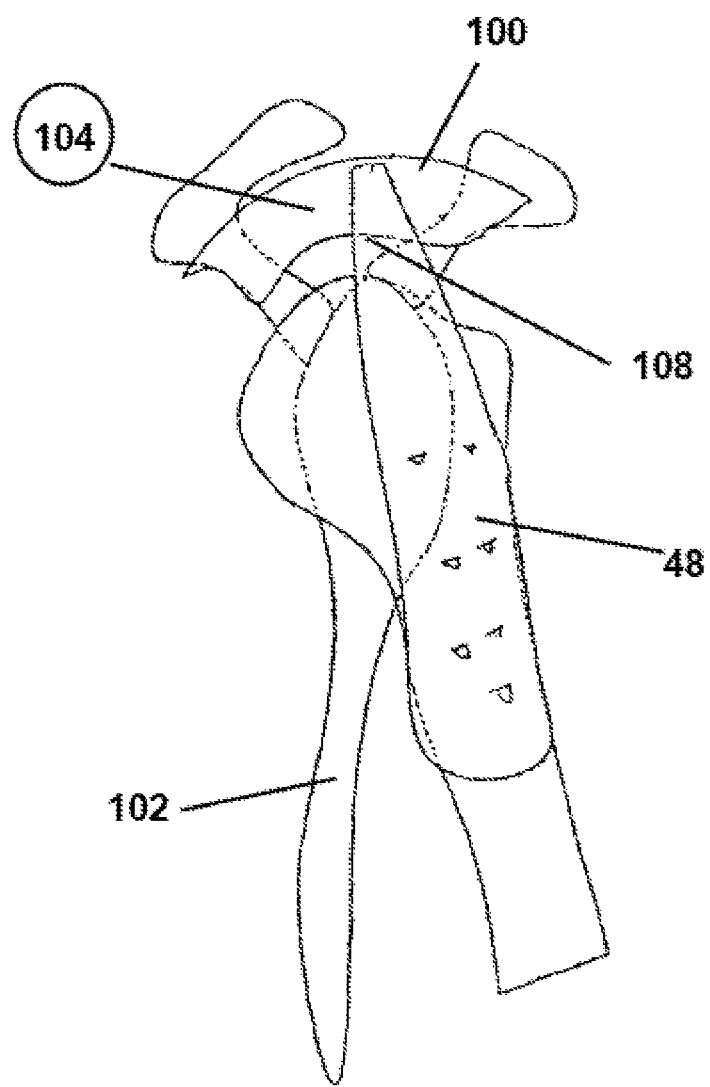
FIG. 17 is a side view of FIG. 16.

A shoulder prosthesis according to the present invention is shown in FIGS. 16 and 17. A first plate is attached to the top of scapula at the lateral margin. The first plate provides an articulating surface in the form of a recess. A lip extends back over recess to provide a cavity having a curvature. However, the radius of curvature of the first plate's articulating surface is slightly greater than the radius of the native glenoid fossa.

A second plate 48 is attached to proximal end of humerus. The second plate provides an articulating surface which extends up and over the top of outside edge of humerus condyle. The second plate's articulating surface has the same radius of curvature as the first plate's articulating surface but is smaller. This allows the second plate's articulating surface to move with respect to the first plate.

The articulating surfaces cooperate so as to provide a desired angle of motion for the prosthesis.

The radius of curvature of the articulating surfaces is slightly greater than the radius of curvature of the articulating surfaces of the native shoulder joint. This pushes the humerus out laterally with respect to the scapula so as to ensure that the motion of the joint occurs on the articulating surfaces, rather than the articulating surfaces of the native joint. This may assist in keeping the native joints separated from each other.

While embodiments of the invention have been illustrated and described, it is not intended that these embodiments illustrate and describe all possible forms of the invention. The words used in the specification are words of description rather than limitation, and it is understood that various changes may be made without departing from the spirit and scope of the invention.

Aspects of the present invention have been described by way of example only and it should be appreciated that modifications and additions may be made thereto without departing from the scope thereof as defined in the appended claims.

What I claim is:

1. A prosthesis for insertion into a patient's knee joint including
    a first plate configured for fixing to a first bone forming part of the joint, the first plate having a deep surface and a superficial surface, the deep surface being shaped to conform to the shape of a selected one of the antero-lateral and antero-medial surface of a distal femur of the patient, the first plate including an aperture extending from the superficial surface to the deep surface of the first plate,
    wherein the aperture is selectively open at an edge to the perimeter of the first plate to define a channel to facilitate, in use, the insertion of at least a selected one of the medial collateral ligament (MCL) and the lateral collateral ligament (LCL) into the aperture to thereby facilitate the first plate accommodating the selected one of the medial collateral ligament (MCL) and the lateral collateral ligament (LCL).

2. The prosthesis as claimed in claim 1, wherein the first plate is configured for fixing to the antero-lateral margin of the patient's femur or the antero-medial margin of the patient's femur, the prosthesis further comprising a second plate that is configured for fixing to the antero-lateral margin of the patient's tibia or the antero-medial margin of the patient's tibia.

3. The prosthesis as claimed in claim 2, further comprising a third plate and a fourth plate, wherein the third plate is configured for fixing to the other of the antero-lateral margin of the patient's femur or the antero-medial margin of the patient's femur, and further wherein the fourth plate is configured for fixing to the other of the antero-lateral margin of the patient's tibia or the antero-medial margin of the patient's tibia.

4. The prosthesis as claimed in claim 2, wherein the first plate has an articulating surface and the second plate has an articulating surface, and wherein in use the articulating surface of the first plate and the articulating surface of the second plate cooperate with each other to facilitate movement of the patient's femur and tibia relative to each other.

5. The prosthesis as claimed in claim 4, wherein the third plate has an articulating surface and the fourth plate has an articulating surface, and wherein in use the articulating surface of the third plate and the articulating surface of the fourth plate cooperate with each other to facilitate movement of the patient's femur and tibia relative to each other.

6. The prosthesis as claimed in claim 4, wherein the articulating surfaces cooperate with each other to guide movement of the patient's femur and tibia through a desired range of motion.

7. The prosthesis as claimed in claim 6, wherein the desired range of motion corresponds to the range of motion of the native knee joint.

8. The prosthesis as claimed in claim 5, wherein at least one of the articulating surfaces of the first plate, the second plate, the third plate, and the fourth plate is provided by a component attached to the respective plate.

9. The prosthesis as claimed in claim 1, wherein the first plate comprises a first component and a second component which together provide the plate.

10. The prosthesis as claimed in claim 9, wherein the aperture is provided in the first component, and the first component and the second component are configured to attach to each other after the insertion of at least the selected one of the medial collateral ligament (MCL) and the lateral collateral ligament (LCL) into the aperture, so that the second component closes the channel.

11. The prosthesis as claimed in claim 9, wherein the first component and the second component are shaped to collectively define an aperture which extends from a superficial surface to a deep surface of the respective plate and that is configured to, in use, receive the at least a selected one of the medial collateral ligament (MCL) and the lateral collateral ligament (LCL).

12. The prosthesis as claimed in claim 1, wherein each portion of the first plate directly adjacent to the aperture is rigid.

13. The prosthesis as claimed in claim 1, wherein the aperture, once the first plate is fixed to the first bone, encapsulates a root of the selected one of the medial collateral ligament (MCL) and the lateral collateral ligament (LCL).

14. The prosthesis as claimed in claim 4, wherein the aperture is spaced apart from the articulating surface of the first plate.

* * * * *